(12) United States Patent
Ribeiro Salvador et al.

(10) Patent No.: US 8,969,395 B2
(45) Date of Patent: Mar. 3, 2015

(54) TRITERPENOID DERIVATIVES USEFUL AS ANTIPROLIFERATIVE AGENTS

(75) Inventors: Jorge Antonio Ribeiro Salvador, Coimbra (PT); Rita Catarina Mendes Dos Santos, Leiria (PT); Marta Cascante Serratosa, Barcelona (ES)

(73) Assignee: Universidade de Coimbra, Coimbra (PT)

( * ) Notice: Subject to any disclaimer, the term of this patent is extended or adjusted under 35 U.S.C. 154(b) by 91 days.

(21) Appl. No.: 13/321,269

(22) PCT Filed: May 20, 2010

(86) PCT No.: PCT/PT2010/000021
§ 371 (c)(1),
(2), (4) Date: Feb. 7, 2012

(87) PCT Pub. No.: WO2010/134830
PCT Pub. Date: Nov. 25, 2010

(65) Prior Publication Data
US 2012/0129901 A1    May 24, 2012

(30) Foreign Application Priority Data
May 20, 2009   (PT) ........................................ 104607

(51) Int. Cl.
| A61K 31/56 | (2006.01) |
| C07J 53/00 | (2006.01) |
| A61K 31/4166 | (2006.01) |
| A61K 31/4178 | (2006.01) |
| A61K 31/4196 | (2006.01) |
| C07D 233/60 | (2006.01) |
| C07D 249/08 | (2006.01) |
| C07J 63/00 | (2006.01) |

(52) U.S. Cl.
CPC ............ C07D 233/60 (2013.01); C07D 249/08 (2013.01); C07J 63/008 (2013.01)
USPC ........ 514/383; 514/396; 514/397; 548/266.2; 548/313.7; 548/334.1

(58) Field of Classification Search
CPC .............. A61K 31/41; A61K 31/4196; A61K 31/4178; A61K 31/4164; C07D 233/60; C07D 233/64; C07D 249/14
USPC ............ 514/383, 397, 398; 548/313.7, 266.2, 548/334.1, 255.8
See application file for complete search history.

(56) References Cited

U.S. PATENT DOCUMENTS

| 7,410,958 B2 * | 8/2008 | Krasutsky et al. | 514/169 |
| 2005/0014730 A1 * | 1/2005 | Carlson et al. | 514/169 |
| 2007/0232577 A1 * | 10/2007 | Xu et al. | 514/169 |
| 2009/0062243 A1 * | 3/2009 | Koohang et al. | 514/169 |

FOREIGN PATENT DOCUMENTS

WO    WO 2007/112043    10/2007

OTHER PUBLICATIONS

Ye, Wencai et al. (AN 2011:829635, HCAPLUS, DN 155:123587, abstract of CN 102108092, Jan. 29, 2011).*
Antimonova, A.N. et al., "Synthesis of betulonic acid amides", Chemistry of Natural Compounds, Coden: CHNCA 8, ISSN: 0009-3130, vol. 44, No. 3, 2008, pp. 327-333.
Liby, K. et al., "Novel semisynthetic analogues of betulinic acid with diverse cytoprotective, anti proliferative and proapoptotic activities", Molecular Cancer Therapeutics, vol. 6, No. 7, Jul. 2007, pp. 2113-2119.
Santos RC et al., "Novel semisynthetic derivatives of betulin and betulinic acid with cytotoxic activity", Bioorganic & Medicinal Chemistry, vol. 17, No. 17, Sep. 1, 2009.
International Search Report for International Patent Application No. PCT/PT2010/000021 dated Oct. 4, 2010.

* cited by examiner

*Primary Examiner* — Sabiha N Qazi
(74) *Attorney, Agent, or Firm* — Pearl Cohen Zedek Latzer Baratz LLP

(57) ABSTRACT

Formula (I) and (II). The present invention relates to the use of a new lupane derivative of general formula (I) or (II), or a pharmaceutically acceptable salt, crystal form, complex, hydrate, or hydrolysable ester thereof, for preventing and/or inhibiting tumor growth and for treating cancer and other proliferative diseases, more particularly for treating leukemia, liver, cervical, colon and prostate cancer. The present invention also relates to the synthesis of these compounds and to pharmaceutical compositions which contain them.

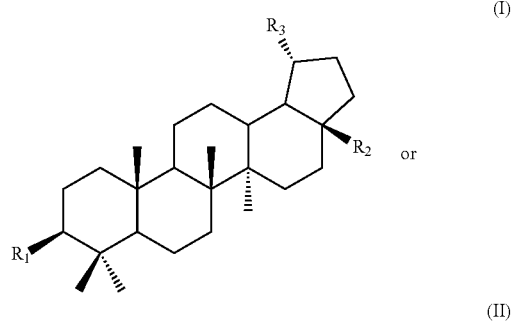

(I)

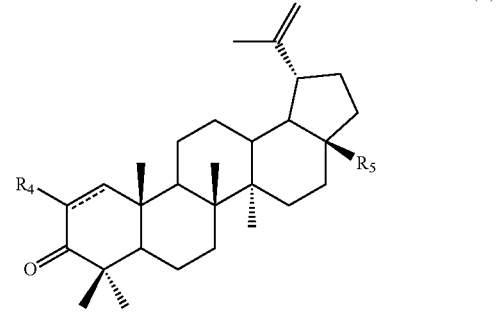

(II)

2 Claims, 8 Drawing Sheets

Betulin 1: R = CH$_2$OH

Betulinic acid 2: R = COOH

TRITERPENOID DERIVATIVES USEFUL AS ANTIPROLIFERATIVE AGENTS

FIELD OF THE INVENTION

The present invention relates to novel betulin and betulinic acid derivatives and processes for preparation of such derivatives. This invention also relates to the field of cancer treatment and is based on the discovery that these novel betulin and betulinic acid derivatives are potent anti-tumor agents.

BACKGROUND OF THE INVENTION

Today cancer is the second most important disease leading to death in the developing and developed countries. Cancer claims over six million lives globally each year. Although the efficacy of chemotherapy and other standard therapies for the majority of cancer types has been improved during the last decades, the treatment of most human malignances is still facing high mortality rates. Moreover, toxic side effects of the current chemotherapeutical drugs are often causing a severe reduction in the quality of life. Therefore, the development of novel potent, but non-toxic anti-cancer agents is worth a continuous effort. It was been discovered, that several plant derived natural products may serve as effective anticancer drugs, among them are plant triterpenes, for example betulin and betulinic acid (Setzer, W. N. and Setzer, M. C., Mini-Rev. Med. Chem., 3:540-556, 2003 and Kinghorn, A. D. et al., Planta Med., 70:691-705, 2004). Betulin is present in large quantities in the outer birch bark of numerous species of birch trees. For example the outer bark of *Betula paparifera* contains nearly 5-18% betulin (U.S. patent Ser. No. 09/371,298). Betulinic acid can also derive from several natural sources (U.S. Pat. Nos. 6,264,998, 6,175,035 and 6,943,260 and WO 03/066659) or it can be chemically derived from betulin. Pezzuto, J. M. et al., (U.S. Pat. No. 5,804,575) disclosed two processes for the synthesis of betulinic acid from betulin. Krasutsky, P. A. et al., (U.S. Pat. No. 6,232,481) disclosed a further multi-step process for the synthesis of this triterpenoid. Finally, Menard, H. et al., (WO 2006/063464) also reported the synthesis of betulinic acid from betulin with an electrochemical oxidation reaction. Both betulin and betulinic acid were reported to display several biological effects including anti-inflammatory, antiviral, antimalarial, anticancer, antiseptic, antimicrobial and antifeedant activities (Dzubak, P. et al., Nat. Prod. Rep., 23:294-311, 2006 and Tolstikova, T. G. et al., Russ. J. Bioorg. Chem., 32:37-49, 2006). However amongst all the aforementioned activities, betulinic acid has been found to exhibit particular anticancer and anti-HIV activities (WO 98/51294, U.S. Pat. No. 5,869,535, US 2006/0159783, WO 96/39033 and U.S. Pat. No. 5,679,828). Betulinic acid was originally considered a melanoma-specific cytotoxic agent. Pisha, E. et al., (Nat. Med., 1:1046-1051, 1995) reported that betulinic acid has an unexpected selective antitumor activity against human melanoma cells, MEL-1, MEL-2, and MEL-4 and confirmed this effectiveness using athymic mice. DasGupta, T. K. et al. and Pezzuto, J. M et al., (WO 96/29068 and U.S. Pat. No. 5,962,527) also disclosed that betulinic acid and its derivatives are useful on treatment of human melanoma. However recent evidence indicates that betulinic acid possesses a broader spectrum of cytotoxic activity against other cancer cell lines. Ramadoss, S. et al. (U.S. Pat. No. 6,048,847) reported for the first time the anti-leukemia, anti-lymphoma, anti-prostate cancer and anti-lung cancer activity of betulinic acid and its derivatives. Debatin, K. M. et al. (U.S. Pat. No. 6,369,109) reported the activity of betulinic acid and derivatives against neuroblastoma cells and Mukherjee, R. et al. (US 2006/0159783) reported the anticancer activity of betulinic acid against cancers of colon, intestine, stomach, breast, lung, cervix, ovary, prostate, oral cavity, larynx, liver, pancreas, kidney, bladder, endothelial cells, glioblastoma, leukemia and myeloma, using a herbal extract rich in this triterpenoid. The molecular mechanism of betulinic acid effects on cancer cells is still subject of continuous investigations. However, this compound seems to induce apoptosis via the activation of caspases, independent of cellular p53 genes status and CD95 activation, (Fulda, S. et al., Cancer Res., 57:4956-4964, 1997 and Wick, W. et al., J. Pharmacol. Exp. Ther., 289:1306-1312, 1999), by a direct effect on mitochondria (Fulda, S. et al., J. Biol. Chem., 273:33942-33948, 1998). The apoptosis inducing ability, the apparent lack of toxicity on normal cells (Zuco, V. et al., Cancer Lett., 175:17-25, 2002), and the favorable therapeutic index, have made betulinic acid an attractive and a very promising anticancer agent (Eiznhamer, D. A. and Xu, Z.-Q., IDrugs, 7:359-373, 2004). In the past few years, there has been a great deal of interest in the synthesis and evaluation of new derivatives of betulin and betulinic acid for their biological activities. The structure of betulin and betulinic acid is based on a 30-carbon skeleton which has three sites available for simple chemical modifications C-3, C-20 and C-28. Modifications of the parent structure of these compounds at these positions can produce potentially important derivatives, more effective compared with the starting ones, which may be developed as antitumor drugs. For instance, the use of betulin, betulinic acid and derivatives thereof for cancer chemoprevention and chemotherapy is described in US 2002/0652352, US 2006/0194774, WO 2007/101873, WO 2007/112043, WO 2008/063318, US 2008/0293682, US 2008/0167254 among others. Although, all the above mentioned reports collectively disclose a large number of betulin and betulinic acid derivatives, a need still exists for new derivatives, which are not only potent, but also clinically safe and moreover, have better pharmacokinetic properties. Thus, an object of this invention is the synthesis of new betulin and betulinic acid derivatives that specifically treat, prevent, inhibit, regulate and/or modulate cancer. Nitrogen-containing derivatives of betulin and betulinic acid, such as amine derivatives, oxime derivatives, amino acid conjugates, amide derivatives, hydrazine and hydrazone derivatives, imidazolyl derivatives, and other N-heterocyclic derivatives have been reported to possess antiproliferative effect against tumor cell lines (U.S. Pat. No. 5,869,335, WO 2007/101873, WO 2007/112043 and US 2008/0293682). In our efforts to find molecules which are not only potent therapeutically but also acceptable clinically, we have found that the introduction of an imidazole, methylimidazole or triazole ring at C-3 and C-28 positions of betulin, betulinic acid and several derivatives, provides the desired characteristics which forms the basis of the present invention.

SUMMARY OF THE INVENTION

Figure 1:
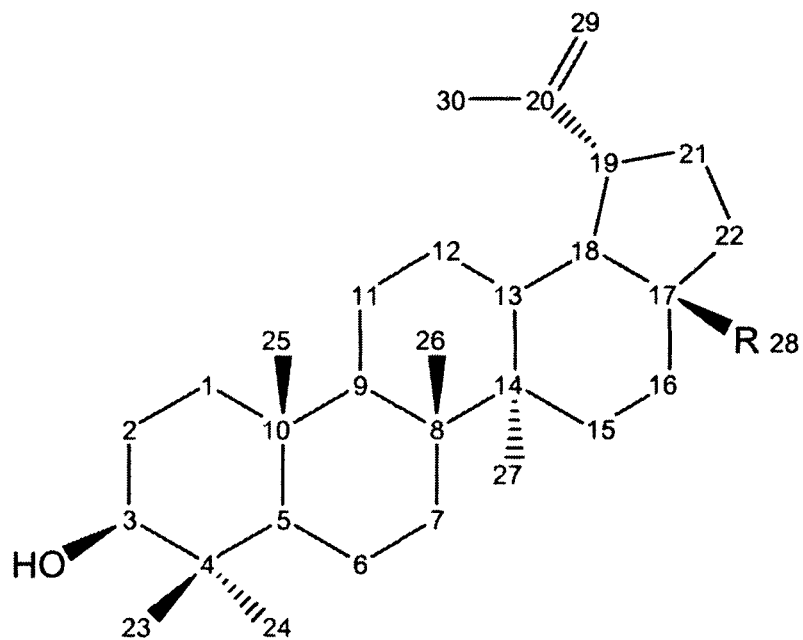
FIG. 1 represents the chemical structure of betulin and betulinic acid.
Figure 2:
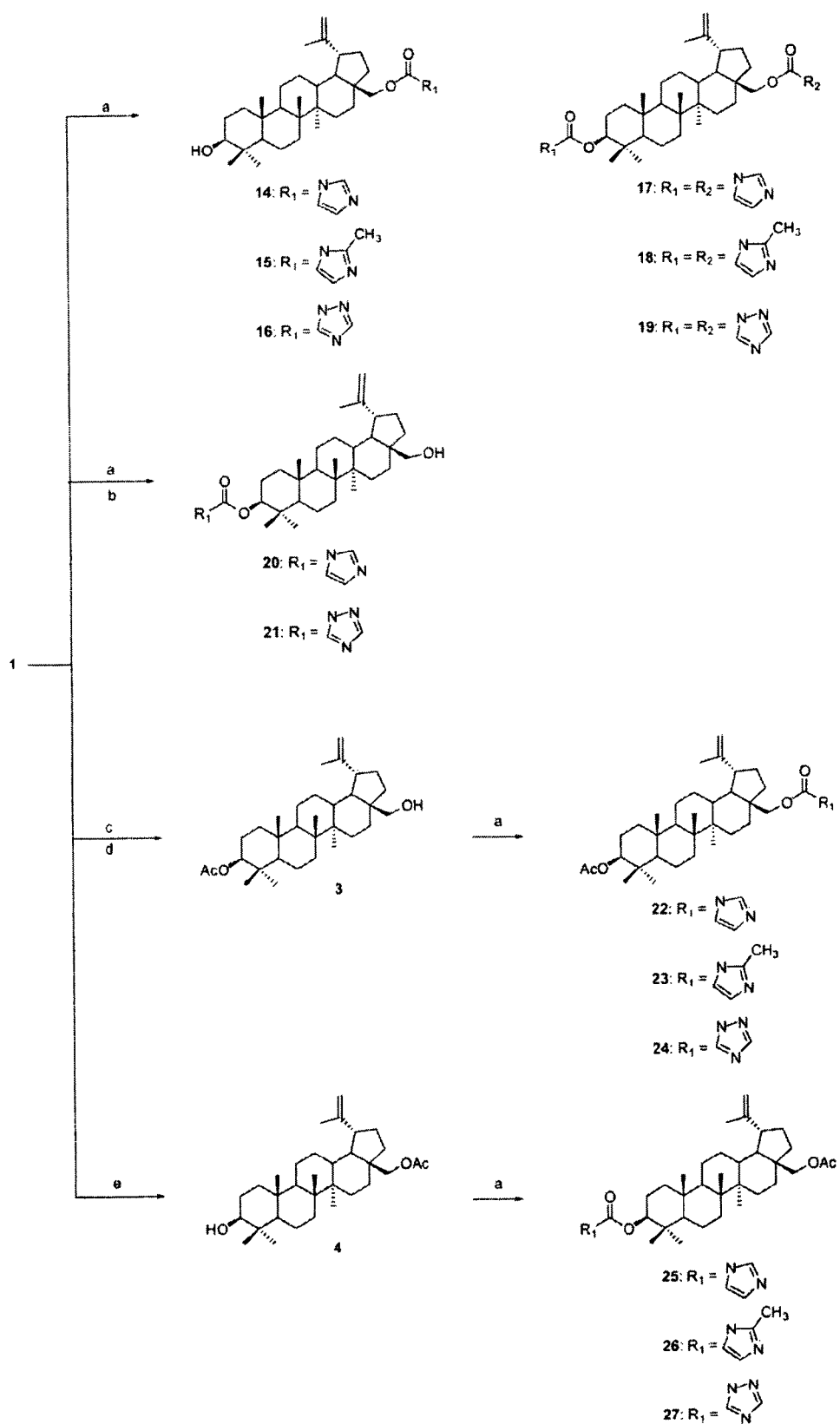
FIG. 2 represents the synthesis and structure of triterpenes and derivatives (3, 4, 14-27). Reagents conditions: (a) CDI, CBMI or CDT, dry THF, $N_2$, reflux in 5-10 h; (b) CDI or CDT, dry THF, $N_2$, reflux in 9-10 h; (c) Silica gel; (d) Acetic anhydride, DMAP, THF, room temperature (rt) in 12 h; (e) KOH, MeOH, THF, rt in 17 h; (f) Acetic anhydride, imidazole, $CHCl_3$, reflux in 2 h.

The present invention relates to betulin and betulinic acid derivatives, compositions comprising betulin and betulinic acid derivatives, use of betulin and betulinic acid derivatives for killing or inhibiting and/or preventing multiplication of cancer cells, a process for the synthesis of these derivatives and testing the bio-activity of the derivatives using cultured human leukemia cells (Jurkat), hepatocellular carcinoma cells (HepG2), colon adenocarcinoma cells (HT-29), cervical adenocarcinoma cells (HeLa), prostate adenocarcinoma cells (PC-3, LNCaP, LAPC4), breast adenocarcinoma cells (MCF-7) melanoma cells (A-370), pancreas carcinoma cells (MIA PaCa-2) and neuroblastoma cells (SH-SY5Y). These new derivatives of betulin and betulinic acid have broad-spectrum anticancer effects, primarily mediated by the inhibition of the cell cycle and induction of the apoptosis of cancer cells. The invention also provides a method for treatment of a patient suffering from cancer. The method comprises administering a therapeutically effective dose of betulin or betulinic acid derivatives in a pharmaceutical composition containing the compounds so as to kill, inhibit or prevent the multiplication of cancer cells. In a preferred embodiment, pharmaceutically acceptable carriers, diluents, excipients and/or solvents are used with betulin and betulinic acid derivatives. The method of treatment of the present invention may be particularly useful in the treatment of hepatocellular carcinoma, cervical adenocarcinoma, leukemia, prostate adenocarcinoma and colon adenocarcinoma. More specifically, one aspect of the present invention provides a compound of formula (I) or (II):

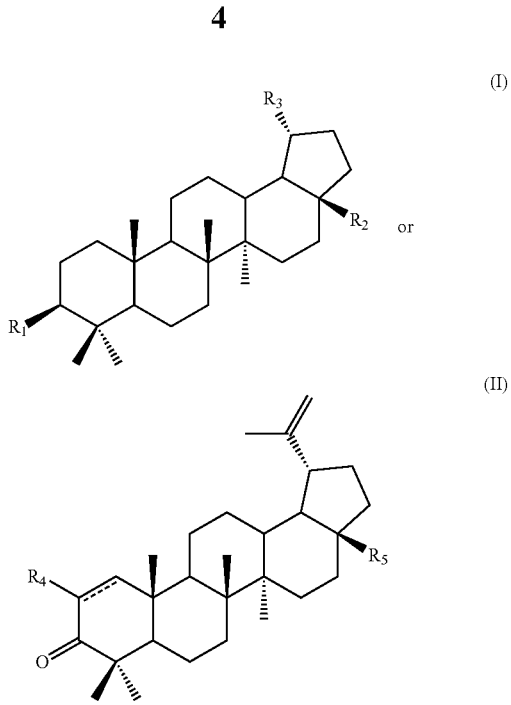

or a pharmaceutically acceptable salt or solvate thereof wherein, $R_1$ is selected from the group consisting of OH, OAc or $OCOR_6$; $R_2$ is selected from $CH_2OH$, $CH_2OAc$, COOH, COOMe, $CH_2OCOR_6$ or $COR_6$, $R_3$ is selected from $CH_2=CCH_3$, $CH_2=CCH_2OMe$ or $CH(CH_3)CHO$; ═ is a single or a double bond; $R_4$ is selected from H, OH or $OCOR_6$; $R_5$ is selected from COOH or $COR_6$; $R_6$ is a five membered aromatic heterocyclic selected from imidazolyl, 2-methylimidazolyl or triazolyl;
with the proviso that the compound of formula (I) is not a compound wherein: $R_1$ is OH, $R_2$ is $CH_2OH$ and $R_3$ is $CH_2=CCH_3$; or $R_1$ is OH, $R_2$ is $CH_2OH$ and $R_3$ is $CH_2=CCH_2OMe$; or $R_1$ is OH, $R_2$ is $CH_2OH$ and R is $CH(CH_3)CHO$; or $R_1$ is OH, $R_2$ is COOH and $R_3$ is $CH_2=CCH_3$; or $R_1$ is OH, $R_2$ is COOH and $R_3$ is $CH_2=CCH_2OMe$; or $R_1$ is OH, $R_2$ is COOH and $R_3$ is $CH(CH_3)CHO$; or $R_1$ is OAc, $R_2$ is COOH and R is $CH_2=CCH_3$; or $R_1$ is OAc, $R_2$ is COOH and $R_3$ is $CH_2=CCH_2OMe$, or $R_1$ is OAc, $R_2$ is COOH and $R_3$ is $CH(CH_3)CHO$; or $R_1$ is OH, $R_2$ is COOMe and $R_3$ is $CH_2=CCH_3$; or $R_1$ is OH, $R_2$ is COOMe and $R_3$ is $CH_2=CCH_2OMe$; or $R_1$ is OH, $R_2$ is COOMe and $R_3$ is $CH(CH_3)CHO$; or $R_1$ is OAc, $R_2$ is COOMe and $R_3$ is $CH_2=CCH_3$; or $R_1$ is OAc, $R_2$ is COOMe and $R_3$ is $CH_2=CCH_2OMe$; or $R_1$ is OAc, $R_2$ is COOMe and $R_3$ is $CH(CH_3)CHO$; or $R_1$ is OH, $R_2$ is $CH_2OAc$ and $R_3$ is $CH_2=CCH_3$; or $R_1$ is OH, $R_2$ is $CH_2OAc$ and $R_3$ is $CH_2=CCH_2OMe$; or $R_1$ is OH, $R_2$ is $CH_2OAc$ and $R_3$ is $CH(CH_3)CHO$; or $R_1$ is OAc, $R_2$ is $CH_2OH$ and $R_3$ is $CH_2=CCH_3$; or $R_1$ is OAc, $R_2$ is $CH_2OH$ and $R_3$ is $CH_2=CCH_2OMe$, or $R_1$ is OAc, $R_2$ is $CH_2OH$ and $R_3$ is $CH(CH_3)CHO$; or $R_1$ is OAc, $R_2$ is $CH_2OAc$ and $R_3$ is $CH_2=CCH_3$; or $R_1$ is OAc, $R_2$ is $CH_2OAc$ and $R_3$ is $CH_2=CCH_2OMe$; or $R_1$ is OAc, $R_2$ is $CH_2OAc$ and $R_3$ is $CH(CH_3)CHO$, or a pharmaceutically acceptable salt thereof;
and with the proviso that the compound of formula (II) is not a compound wherein ═ is a single bond, $R_4$ is H and $R_5$ is COOH; or ═ is a double bond, $R_4$ is H and $R_5$ is COOH; or ═ is a double bond, $R_4$ is OH and $R_5$ is COOH, or a pharmaceutically acceptable salt thereof.

Another aspect of the present invention provides a compound of formula (I) or (II) or a pharmaceutically acceptable salt or solvate thereof for administration to a patient suffering from cancer selected from the group consisting of hepatocellular carcinoma, cervical adenocarcinoma, leukemia, prostate adenocarcinoma and colorectal adenocarcinoma.

The preferred compounds that are encompassed under formula (I) are summarized in Table 1:

TABLE 1

The representative compounds encompassed under formula (I)

| Compounds | R$_1$ | R$_2$ | R$_3$ |
|---|---|---|---|
| 14 | OH | 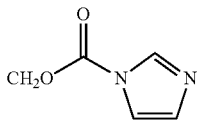 | CH$_2$=CCH$_3$ |
| 15 | OH | 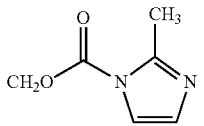 | CH$_2$=CCH$_3$ |
| 16 | OH | 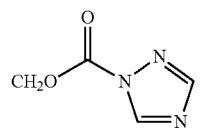 | CH$_2$=CCH$_3$ |
| 17 | 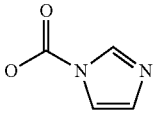 | 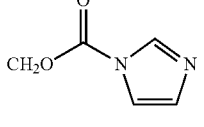 | CH$_2$=CCH$_3$ |
| 18 | 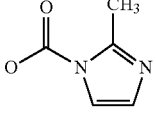 | 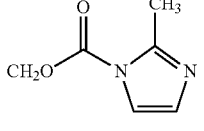 | CH$_2$=CCH$_3$ |
| 19 | 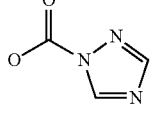 | 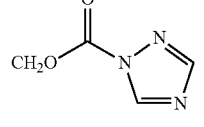 | CH$_2$=CCH$_3$ |
| 20 | 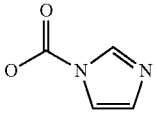 | CH$_2$OH | CH$_2$=CCH$_3$ |
| 21 | 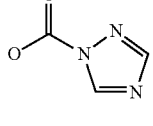 | CH$_2$OH | CH$_2$=CCH$_3$ |
| 22 | OAc | 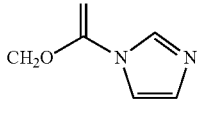 | CH$_2$=CCH$_3$ |
| 23 | OAc | 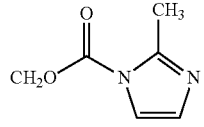 | CH$_2$=CCH$_3$ |
| 24 | OAc | 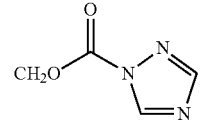 | CH$_2$=CCH$_3$ |
| 25 | 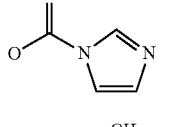 | CH$_2$OAc | CH$_2$=CCH$_3$ |
| 26 | 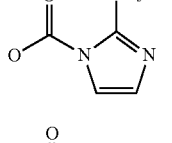 | CH$_2$OAc | CH$_2$=CCH$_3$ |
| 27 | 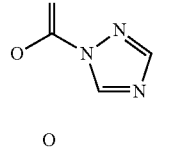 | CH$_2$OAc | CH$_2$=CCH$_3$ |
| 28 | 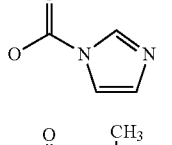 | COOH | CH$_2$=CCH$_3$ |
| 29 | 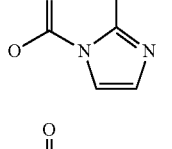 | COOH | CH$_2$=CCH$_3$ |
| 30 | 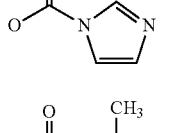 | 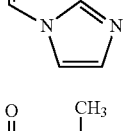 | CH$_2$=CCH$_3$ |
| 31 | 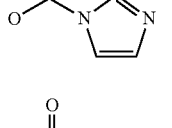 | 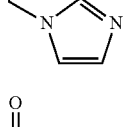 | CH$_2$=CCH$_3$ |
| 32 | 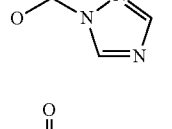 | 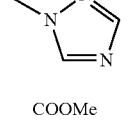 | CH$_2$=CCH$_3$ |
| 33 | 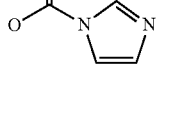 | COOMe | CH$_2$=CCH$_3$ |

TABLE 1-continued

The representative compounds encompassed under formula (I)

| Compounds | R₁ | R₂ | R₃ |
|---|---|---|---|
| 34 | 2-methylimidazole-N-carbonyloxy | COOMe | CH₂=CCH₃ |
| 35 | OH | CH₂O-C(O)-imidazol-N-yl | CH₂=CCH₂OMe |
| 36 | OH | CH₂O-C(O)-(2-methylimidazol-N-yl) | CH₂=CCH₂OMe |
| 37 | OH | CH₂O-C(O)-(1,2,4-triazol-N-yl) | CH₂=CCH₂OMe |
| 38 | imidazole-N-carbonyloxy | CH₂O-C(O)-imidazol-N-yl | CH₂=CCH₂OMe |
| 39 | 2-methylimidazole-N-carbonyloxy | CH₂O-C(O)-(2-methylimidazol-N-yl) | CH₂=CCH₂OMe |
| 40 | 1,2,4-triazole-N-carbonyloxy | CH₂O-C(O)-(1,2,4-triazol-N-yl) | CH₂=CCH₂OMe |
| 41 | OH | CH₂O-C(O)-imidazol-N-yl | CH(CH₃)CHO |
| 42 | OH | CH₂O-C(O)-(2-methylimidazol-N-yl) | CH(CH₃)CHO |
| 43 | imidazole-N-carbonyloxy | CH₂O-C(O)-imidazol-N-yl | CH(CH₃)CHO |

The preferred compounds that are encompassed under formula (II) are summarized in Table 2:

TABLE 2

The representative compounds encompassed under formula (II)

| Compounds | R₄ | R₅ | ----- |
|---|---|---|---|
| 44 | H | imidazole-N-carbonyl (CHO-imidazol-N-yl) | — |
| 45 | H | 2-methylimidazole-N-carbonyl | — |
| 46 | H | imidazole-N-carbonyl | = |
| 47 | H | 2-methylimidazole-N-carbonyl | = |
| 48 | OH | imidazole-N-carbonyl | = |
| 49 | imidazole-N-carbonyloxy | imidazole-N-carbonyl | = |
| 50 | 2-methylimidazole-N-carbonyloxy | COOH | = |

The present invention provides novel betulin and betulinic acid derivatives of formulas (I) and (II) exhibiting useful activity in inhibition of cancer cell growth. In particular, the present invention is directed to inhibiting, malignant tumor growth associated with hepatocellular carcinoma, cervical adenocarcinoma, leukemia, prostate adenocarcinoma and colorectal adenocarcinoma. The improved, cytotoxicity profile renders to the novel betulin and betulinic acid derivatives of formulas (I) and (II) of this invention superior candidates for treatment cancer.

In another aspect, the present invention provides a process of preparation of novel betulin and betulinic acid derivatives of formulas (I) and (II), that have activity against cancer cells, and that have physical properties that make the derivatives easier to incorporate into compositions that can be administered to a patient for the prevention or inhibition of cancer cell growth.

Still another aspect of the present invention is to overcome the problem of insufficient availability associated with synthetic anticancer agents by utilizing readily available, and naturally occurring betulin, betulinic acid or a derivative thereof.

Another aspect of the present invention is to overcome the problem of high mammalian toxicity associated with synthetic anticancer agents by using a derivative of a natural compound, e.g. betulin and betulinic acid.

Another aspect of the present invention is to overcome the problem of high cost of synthetic anticancer agents by utilizing the readily available natural product derived compound, e.g. betulin and betulinic acid and its derivatives which are expected to be less expensive than other chemotherapeutic drugs.

In a further aspect, the present invention provides a method of identifying a tumor amenable to treatment with the compound of the present invention, consisting of contacting a sample of the cells with the compound, wherein $IC_{50}$ of the compound against the sample of cells that is smaller than or equal to 30 μM in is indicative that the tumor is amenable to treatment with the said compound.

Another aspect of the present invention provides a method for administering a compound of the present invention to a patient suffering from cancer selected from the group consisting of hepatocellular carcinoma, cervical adenocarcinoma, leukemia, prostate adenocarcinoma and colon adenocarcinoma.

In yet another aspect of the present invention, concerns a pharmaceutical composition comprising the compounds of formulas (I) and (II) and a pharmaceutically acceptable diluent, carrier or excipient.

In accordance to another aspect the present invention provides a method for treating cancer in a patient. The method comprises administering a pharmacologically effective amount of one of the betulin and betulinic acid derivative compounds described herein to the patient where the compounds inhibit growth of cancer cells thereby treating the cancer.

In another aspect, the present invention provides novel betulin and betulinic acid derivatives, which are used for inhibiting cell cycle and inducing apoptosis.

These and other aspects of the present invention will become apparent from the following description of the invention, which are intended to limit neither the spirit or scope of the invention but are only offered as illustrations of the preferred embodiments of the invention.

DETAILED DESCRIPTION OF THE INVENTION

The term "pharmaceutical acceptable salts" as used herein refers to compounds described herein, wherein the parent compound is modified by making acid or base salts thereof. Examples of pharmaceutical acceptable salts include but are not restricted to specific ones inasmuch as they are currently used in foods and beverages and medicinal or pharmaceutical compositions. Specific examples thereof include alkali metal salts such as calcium, magnesium, barium, zinc, sodium and potassium salts; halides and aluminium salts, alkylamine, salts such as salts with, for instance, ammonia, methylamine, dimethylamine, trimethylamine, ethylamine, diethylamine, triethylamine, propylamine, butylamine, tetrabutylamine, pentyl amine and hexylamine, alkanolamine salts such as salts with for instance, ethanolamine, diethanolamine, triethanolamine, propanolamine, dipropanolamine, isopropanolamine and diisopropanolamine; salts with other organic amines such as piperazine and piperidine; salts with basic amino acids such as lysine, arginine, histidine, tryptophan and guanidine; and other salts such as acetate, ascorbate, benzoate, citrate, oxalate, sterate, trifluoracetate, succinate, tartarate, lactate, fumarate, gluconate, glutamate, phosphate/ diphosphate and valerate. Generally these salts can be prepared by reacting the free acid or base forms of these compounds with a stoichiometric amount of the appropriate base or acid in water or in an organic solvent or in a mixture of two. Lists of suitable salts are found in Remington's Pharmaceutical Sciences $17^{th}$ ed. Mack Publishing Company, Easton, Pa., 1985. On the whole, these salts have solubility in water higher than that of the original compounds.

As used herein the term "contacting" refers to any suitable method of bringing betulin, betulinic acid, their derivatives and analogs or any other therapeutic compound into contact with a cell, preferably an abnormally proliferating cell. In vitro this is achieved by exposing the cells to the inhibitory agents in a suitable medium.

A "pharmacological effective amount" or "therapeutically effective amount" refers to an amount effective, at dosages and for periods of time necessary, to achieve the desired therapeutic result, such as a reduction of tumor cells growth.

The term "treating cancer" or "treatment of cancer" includes but is not limited to, halting the growth of cancer cells or killing the cancer cells, or reducing the number of cancer cells. Halting the growth refers to halting any increase in the number of cancer cells or halting the division of the cancer cells.

As would be apparent to one of ordinary skills in the art, the term "cancer" or "cancer cells" or "tumor" refers to examples of neoplastic cell proliferative diseases.

As used herein the term "patient" refers to any target of the treatment.

By the term "normal cell" is meant herein a cell sample that does not contain a specifically chosen cancer. The normal cells used are non tumoral cell lines.

The term "substrate" refers to either betulin or betulinic acid or their intermediate derivatives 3-13 as starting materials.

The compounds of the present invention can be orally or parenterally and stably administered to human and animals to act as, for instance, a drug or a quasi-drug. In this respect, examples of parenteral administration include intravenous injection, intra-arterial injection, intramuscular injection, subcutaneous injection, intracutaneous injection, intraperitoneal injection, intra-spinal injection, peridural injection, percutaneous administration, perpulmonary administration, pernasal administration, perintestinal administration, administration through oral cavity and permucosal administration and examples of dosage forms used in such parenteral administration routes include injections, suppositories (such as rectal suppositories, urethral suppositories and vaginal suppositories), liquids for external use (such as injections, gargles, mouth washes, fomentations, inhalants, sprays, aerosols, enemas, paints, cleaning agents, disinfectants, nasal drops and ear drops), cataplasms, percutaneous absorption tapes, external preparations for the skin, ointments (such as pastes, liniments and lotions). In addition, examples of pharmaceutical preparations for oral administration include tablets for internal use (such as uncoated tablets, sugar-coated tablets, coating tablets, enteric coated tablets and chewable tablets), tablets administered to oral cavity (such as buccal preparations, sublingual tablets, toches and adhesive tablets), powders, capsules (such as hard capsules, and soft capsules), granules (such as coated granules, pills, troches, liquids preparations or pharmaceutically acceptable sustained release pharmaceutical preparations). Specific examples of liquid preparations capable of being orally administered are solutions for internal use, shake mixtures, suspensions, emulsions, syrups, dry syrups, elixirs, infusions, decoctions and lemonades.

The invention also relates to a pharmaceutical composition comprising the above-mentioned compounds and pharmaceutically acceptable diluents, carriers or excipients. As used herein "pharmaceutically acceptable diluents", "carriers" or "excipients" includes any and all solvents, dispersion media, coatings, antibacterial and antifungal agents, fillers, lubricants, binders, stabilizers and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. Diluents that may be used in the composition include but are not limited to dicalcium phosphate, calcium sulphate, lactose, cellulose, kaolin, mannitol, sodium chloride, dry starch, powdered sugar and for prolonged release tablet hydroxy propyl methyl cellulose (HPMC). The binders that may be used in the composition include but are not limited to starch, gelatin and fillers such as sucrose, glucose, dextrose and lactose. Stabilizers used are polysaccharides such as acacia, agar, alginic acid, guar gum and tragacanth, amphotsics such as gelatin and synthetic and semi-synthetic polymers such as carbomer resins, cellulose ethers and carboxymethyl chitin. Excipients that may be used in the compositions include but are not limited to microcrystalline cellulose, calcium sulfate, dicalcium phosphate, starch, magnesium stearate, lactose and sucrose. Solvents that may be used include but are not limited to Ringers solution, water, distilled water, dimethyl sulfoxide to 50% in water, propylene glycol (neat or in water), phosphate buffered saline, balanced salt solution, glycol and other conventional fluid. The use of such media and agents for pharmaceutically active substances is well known in the art (Rowe, R. C. et al., Handbook of pharmaceutical excipients, 4$^{th}$ edition, Pharmaceutical Press, London UK, 2003). Supplementary active compounds can also be incorporated into the compositions.

Pharmaceutical compositions within the scope of the present invention desirably contain the active agent (the above mentioned compound) in an amount effective to achieve the desired therapeutic effect while avoiding adverse side effects. Pharmaceutically acceptable preparations and salts of the active agent are within the scope of the present invention are well known in the art. The amount of the therapeutic or pharmaceutical composition which is effective in the treatment of a particular disease, disorder or condition will depend on the nature and severity of the disease, the target site of action, the patient's weight, special diets being followed by the patient, concurrent medications being used, the administration route and other factors that will be recognized by those skilled in the art. The dosage will be adapted by the clinician in accordance with conventional factors such as extent of the disease and different parameters from the patient. The pharmaceutical compositions of the present invention can be delivered in a controlled release system. For example, polymeric materials can be used (Smolen, V. F. and Ball, L., Controlled Drug Bioavailability: Drug product design and performance, Wiley & Sons, 1984; Ranade V. V. and Hollinger, M. A., Drug Delivery Systems (Pharmacology & Toxicology Series), 2$^{nd}$ edition, CRRC Press, 2003), or a pump may be used (Saudek, C. D et al., N. Engl. J. Med. 321:574-579, 1989). Compounds of the present invention may also be delivered by the use of monoclonal antibodies as individual carriers to which the compound molecules are coupled. The compounds of the present invention may also be coupled to a class of biodegradable polymers useful in achieving controlled release of the drug, for example polylactic acid, polyorthoesters, cross-linked amphipathic block copolymers and hydrogels, polyhydroxy butyric acid and polydihydropyrans. For veterinary use, a compound of the present invention or a nontoxic salt thereof is administered as a suitably acceptable formulation in accordance with normal veterinary practice. The veterinarian can readily determine the dosing, regimen and route of administration that is most appropriate for a particular animal.

In a further aspect, the present invention provides a method of preventing or inhibiting tumor growth consisting of contacting the said cell with a therapeutically effective amount of the above-mentioned compound. The tumors to which the compound of the present invention can be applied include swellings and true tumors including benign and malignant tumors. Specific examples of such tumors are gliomas such as astrocytoma, glioblastoma, medulloblastoma, oligodendroglioma, ependymona and choroid plexus papiloma; cerebral tumors such as meningioma, pituitary adenoma, neurioma, congenital tumor, metastatic cerebral tumor, squamous cell carcinoma, lymphoma, a variety of adenomas and pharyngeal cancers resulted from these adenomas such as epipharyngeal cancer, mesopharyngeal cancer and hypopharyngeal cancer; laryngeal cancer, thymoma; mesothelioma such as pleural mesithelioma, peritoneal mesothelioma and pericardial mesothelioma; breast cancer such as thoracic duct cancer, lobular carcinoma and papillary cancer, lung cancers such as bronchogenic carcinoma, alveolar carcinoma, bronchial adenoma, small cell carcinoma, adenocarcinoma, squamous cell carcinoma, large cell carcinoma and adenosquamous carcinoma; gastric carcinoma; esophageal carcinomas such as cervical esophageal carcinomas, thoracic esophageal carcinomas and abdominal esophageal carcinomas; carcinomas of large intestine such as rectal carcinoma, S-like (sigmoidal) colon carcinoma, ascending colon carcinoma, lateral colon carcinoma, cecum carcinoma and descending colon carcinoma; hepatomas such as hepatocellular carcinoma, intrahepatic hepatic duct carcinoma, hepatocellular blastoma, and hepatic duct cystadenocarcinoma; pancreatic carcinoma; pancreatic hormone-dependent tumors such as insulinoma, gastrinoma, VIP-producing adenoma, extrahepatic hepatic duct carcinoma, hepatic capsular carcinoma, perial carcinoma, renal pelvic and uretal carcinoma; urethral carcinoma; renal cancers such as renal cell carcinoma (Grawitz tumor) Wilms' tumor (nephroblastoma) and renal angiomyolipoma; testicular cancers or germ cell tumors such as seminoma, embryonal carcinoma, vitellicle tumor, choriocarcinoma and teratoma; prostatic cancer, bladder cancer, carcinoma of vulva; hysterocarcinomas such as carcinoma of uterine cervix, uterine corpus cancer and solenoma; hysteromyoma, uterine sarcoma, villous diseases, carcinoma of vagina, ovarian germ cell tumors such as dysgerminoma, vitellicle tumor, premature teratoma, dermoidal cancer and ovarian tumors such as ovarian cancer; melanomas such as nevocyte and melanoma; skin lymphomas such as mycosis fungoides, skin cancers such as endoepidermal cancers resulted from skin cancers, prodrome or the like and spinocellular cancer, soft tissue sarcomas such as fibrous histiocytomayosis, angiosarcoma, liposarcoma, rhabdomyosarcoma, leiomyosarcoma, synovial sarcoma, sarcoma fibroplasticum (fibrosarcoma), neurioma, hemangiosarcoma, fibrosarcoma, neurofibrosarcoma, perithelioma (hemangiopericytoma) and alveolar soft part sarcoma, lymphomas such as Hodgkin lymphoma and non-Hodgkin lymphoma, myeloma, plasmacytoma, acute myelocytic (myeloid) leukemia and chronic myeloid leukemia, leukemia such as adult T-cell leukemic lymphoma and chronic lymphocytic leukemia, chronic myeloproliferative diseases such as true plethora, essential thrombocythemia and idiopathic myelofibrosis, lymph node enlargement (or swelling), tumor of pleural effusion, ascitic tumor, other various kinds of adenomas, lipoma, fibroma, hemangeoma, myoma, fibromyoma and endothelioma.

In another aspect it is contemplated that contacting the cancer cells with one of these compounds is effective to induce cell cycle arrest and apoptosis.

Figure 6:
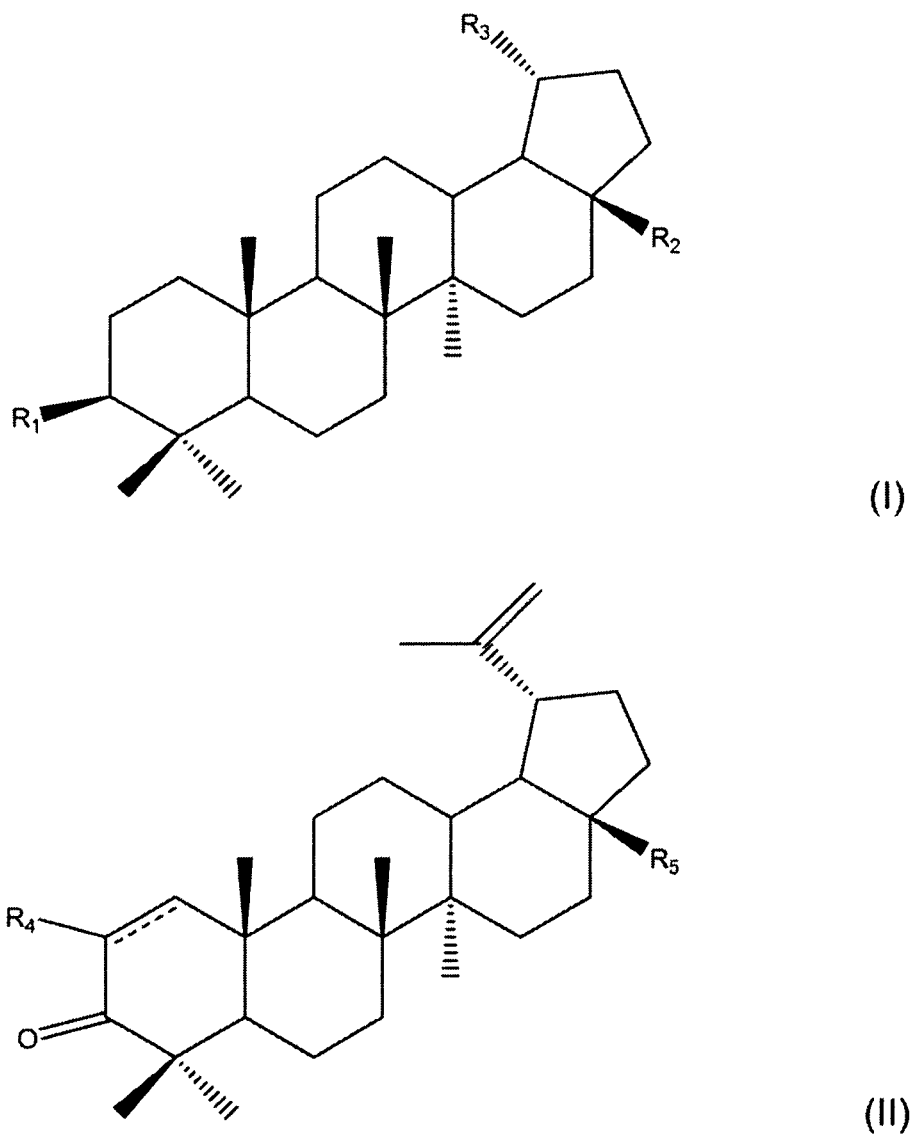
FIG. 6 represents the basics skeletal formulas of derivatives of the present invention.

The methods of preparation of compounds 14-50 of Table 1 and 2 are summarized in the schemes represented in FIG. 2-5. Conventional procedure skilled in the art can be used in the preparation of the various betulin and betulinic acid intermediate derivatives used as substrates. The basics skeletal formulas of the compounds of the invention are represented in FIG. 6. The compounds of the invention are a result of modifications of C-2, C-3, C-20, C-28 or C-29 positions of betulin and betulinic acid. These compounds have been characterized on the basis of spectral data. The pharmaceutical acceptable salts, pharmaceutically acceptable solvates, their isomers, polymorphs, N-oxides and metabolites of these compounds can be prepared by methods known in the art.

Although various embodiments of the invention are disclosed herein, many adaptations and modifications may be made within the scope of the invention in accordance to the common general knowledge of those skilled in this art. Such modifications include the substitution of known equivalents for any aspect of the invention in order to achieve the same result in substantially the same way. The following examples are illustrative of various aspects of the invention, and do not limit the broad aspects of the invention disclosed herein.

Synthesis of Betulin and Betulinic Acid Intermediates

Figure 3:
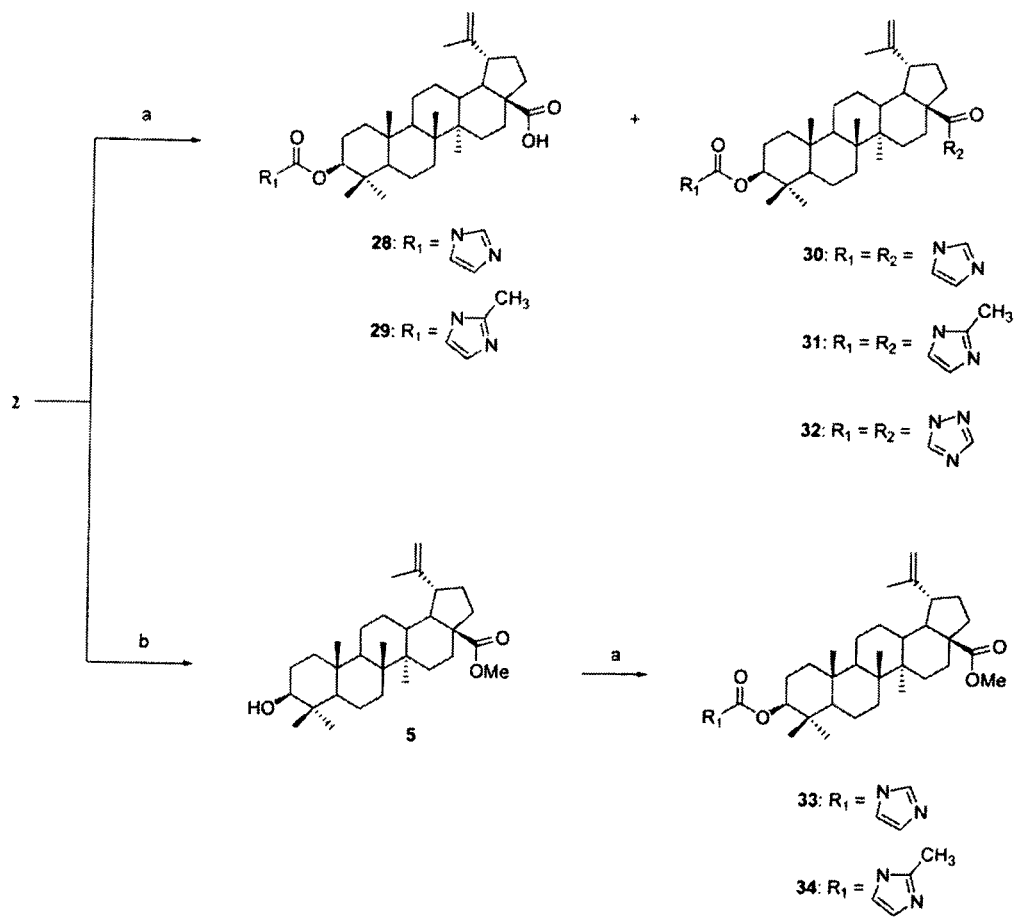
FIG. 3 represents the synthesis and structure of other triterpenes and derivatives (5, 28-34). Reagents conditions: (a) CDI, CBMI or CDT dry THF, $N_2$, reflux in 6-9 h; (b) $CH_3I$, $K_2CO_3$, dry DMF, rt in 1 h.
Figure 4:
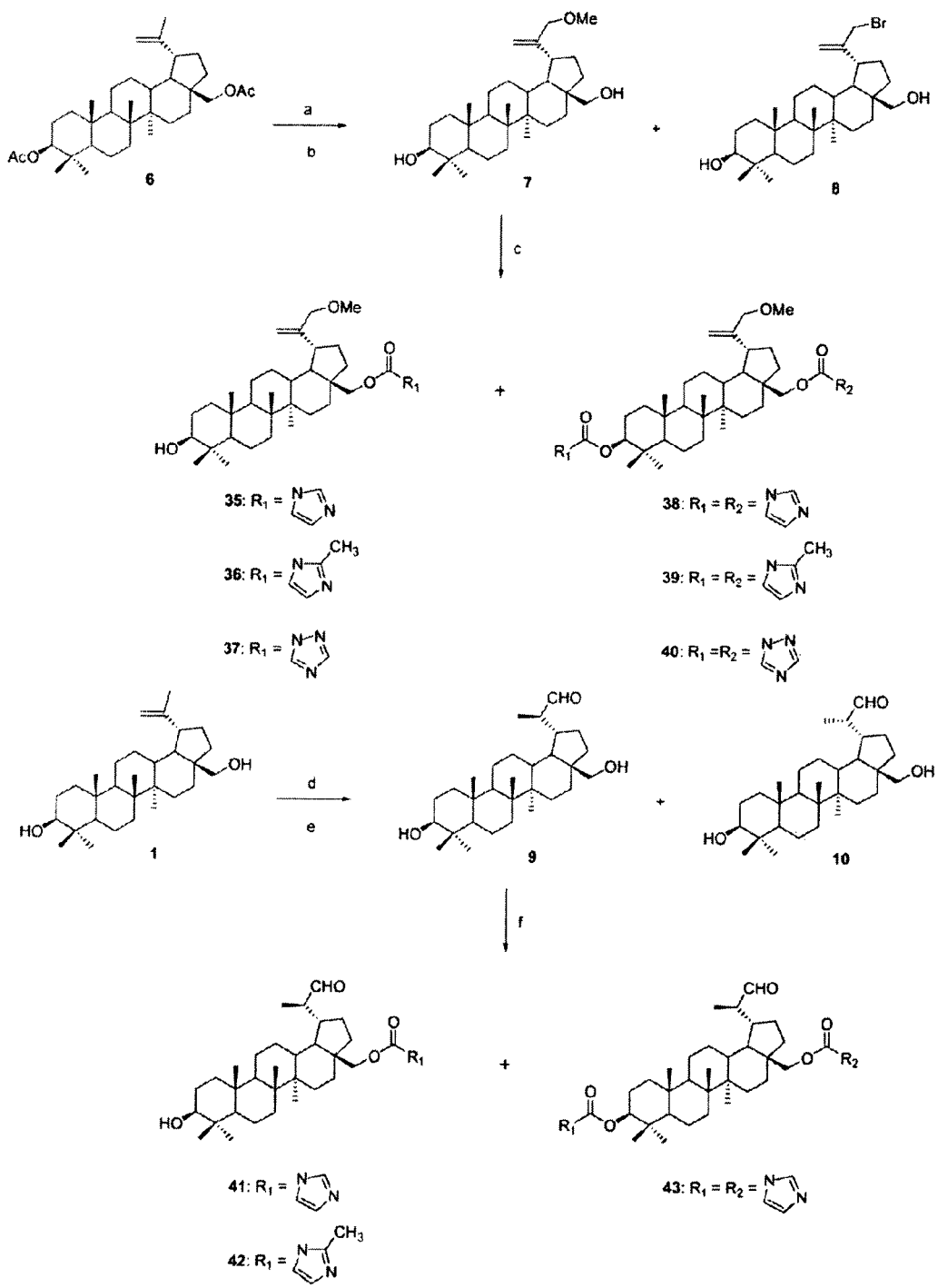
FIG. 4 represents the synthesis and structure of other triterpenes and derivatives (1, 6-10, 35-43). Reagents conditions: (a) NBS, $CCl_4$, reflux in 3 h; (b) NaOH aq. (4N), MeOH, THF, rt in 29 h; (c) CDI, CBMI or CDT, dry THF, $N_2$, reflux in 7-8 h; (d) m-CPBA, $CH_2Cl_2$, 0-5° C. in 5 h; (e) $H_2SO_4$ (2M), 0-5° C., in 1 h; (f) CDI or CBMI, dry THF, $N_2$, reflux in 6-7 h.
Figure 5:
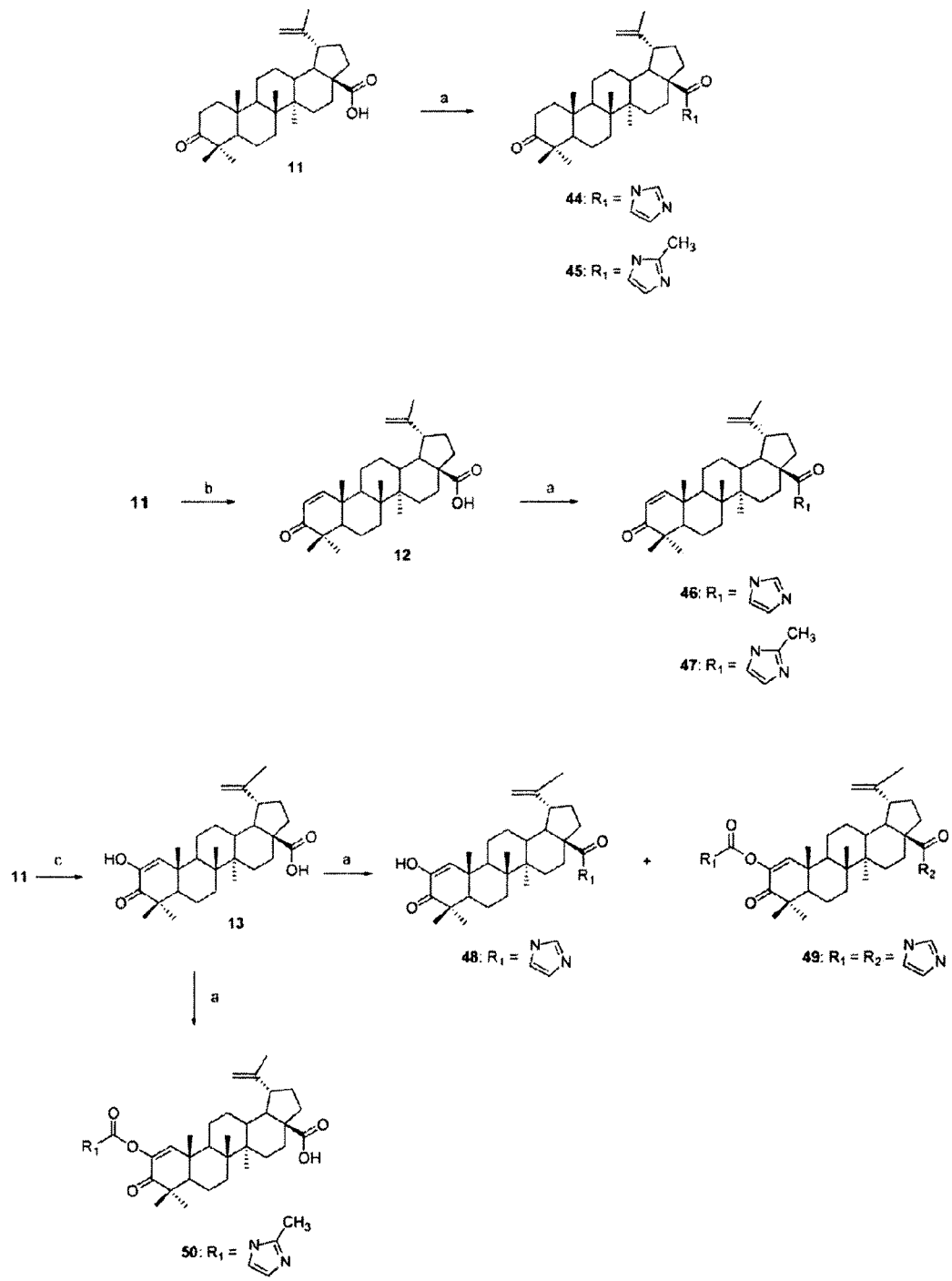
FIG. 5 represents the synthesis and structure of other triterpenes and derivatives (11-13, 44-50) Reagents conditions: (a) CDI or CBMI dry THF, $N_2$, reflux in h; (b) DDQ, dioxane, $N_2$, reflux in 15 h; (c) $O_2$, t-BuOK, t-BuOH, 40° C. in 2 h.

As the reactivity of the C-28 hydroxyl group of betulin 1 is much higher than the one at C-3,28-acetoxybetulin 4 was obtained in moderate yield (78%) by using acetic anhydride ($Ac_2O$) and two equivalents of imidazole in $CHCl_3$, during 2 h period at reflux. Diacetylation of betulin 1 with $Ac_2O$ and a catalytic amount of dimethylaminopyridine (DMAP) in $CH_2Cl_2$ afforded 3β,28-diacetoxybetulin 6 in excellent yield (97%). Subsequent selective hydrolysis of 3β,28-diacetoxybetulin 6 with methanolic potassium hydroxide in THF furnished the 3β-acetoxybetulin. 3 in 74% yield, according to a known procedure (Tietze, L. F. et al., Liebigs Ann. Chem., 12:1245-1249, 1991). As shown in FIG. 3, the methyl ester 5 of the commercial available betulinic acid 2 was synthesized in good yield (83%) by treatment with methyl iodide ($CH_3I$) in the presence of $K_2CO_3$. The methoxylation of the isopropenyl group of betulin 1 occur in two steps as previously described (Uzenkova, N. V. et al., Chem. Nat. Compd., 41:692-700, 2005.) In the first step the reaction of 3β,28-diacetoxybetulin 6 with N-bromosuccinimide (NBS) in $CCl_4$ produced a 30-bromo derivative which was further hydrolyzed by NaOH (4M) in a MeOH:THF mixture at room temperature to afford the 30-methoxy derivative 7 and the 30-bromo derivative 8. The ratio of compounds 7 and 8 depended on the reaction conditions. An increase in the hydrolysis time causes an increase in the amount of the 30-methoxy derivative. For the synthesis of compound 9, betulin 1 was epoxidated with m-chloroperbenzoic acid (m-CPBA), followed by acid catalysed epoxy ring opening to afford the epimeric isomers (20R-aldehyde) 9 (39%) and (20S-aldehyde) 10 (20%) as major products. The downfield shift of the H-20 and H-30 signals in the $^1H$ NMR spectra of the configuration 20R (δ 9.86 and δ 1.10 ppm) in comparison with the configuration 20S (δ 9.62 and δ 1.04 ppm) is characteristic and is consisted with data reported in the literature (Okamoto, I. at al., Chem. Pharm. Bull. 48:120-125, 2000). Betulonic acid. 11 was easily obtained from the well known oxidation with Jone's reagent in acetone (Kim, D. S. H. L. et al., Synth. Commun., 27:1607-1612, 1997). For the synthesis of intermediate 12, betulonic acid 11 was dehydrated with 2,3-dichloro-5,6-dicyanobenzoquinone (DDQ) in dioxane according to the known method (Walker, D.; Hiebert, J. D., Chem. Rev., 67:153-195, 1967). A previously published procedure using oxygen in the presence of potassium tert-butoxide (t-BuOK) was used for the preparation of the diosphenol 13 as major product (72%) (Urban, M. et al., J. Nat. Prod., 67:1100-1105, 2004).

Synthesis of Carbamates and N-Acylimidazoles

The synthesis of the compounds of formulas (I) and (II) were achieved by the reaction of compounds 1-5, 7, 9, 11-13 with 1,1'-carbonyldiimidazole (CDI), 1,1'-carbonylbis(2-methylimidazole) (CBMI) or 1,1'-carbonyldi(1,2,4-triazole) (CDT) at reflux in anhydrous THF under $N_2$ atmosphere. The reaction of CDI with alcohols and phenols has been reported to afford either N-alkylimidazoles or imidazole carboxylic esthers (carbamates), depending both on alcohol structure and on the reaction, conditions used (Tang, Y. Q. et al., Synthesis, 15:2540-2544, 2004). In our case the reaction with CDI., CBMI or CDT afforded the lupane carbamates 14-29, 33-43 and 5.0 in good yields. On the other hand the reaction of CDI, CBMI or CDT with carboxylic acid function of lupane substrates afforded the N-acylheterocyclic derivatives 30-32 and 44-49 which was in accordance with previous results (Rannard, S. P. et al., Org. Lett., 2:2117-2120, 2000).

Materials and Methods

Chemicals

Air and water sensitive reactions were performed under nitrogen atmosphere. Moisture sensitive reagents were introduced via a dry syringe. THF was distilled from $CaH_2$. Betulin (1), Betulinic acid (2), CDI, CBMI, CDT, NBS, NaOH, m-CPBA, $H_2SO_4$, DDQ, t-BuOK and tert-butyl alcohol (t-BuOH) were purchased from Sigma Aldrich Co., whereas the solvents were obtained from VWR Portugal. For thin layer, chromatography (TLC) analysis Kieseigel 60HF254/Kieselgel 60G was used and flash column chromatography (FCC) was performed using Kieseigel 60 (230-400 mesh, Merk). All the chemical yields are not optimized and generally represent the result of the mean of two experiments. Melting points were determined using a BUCHI melting point Point B-540 apparatus and are uncorrected. IR spectra were obtained using a JASCO FT/1R-420 spectrophotometer. NMR spectra were recorder on a Bruker Digital NMR-Avance 300 apparatus and on a Bruker Digital NMR-Avance 400 apparatus in $CDCl_3$ with $Me_4Si$ as the internal standard. Elucidations of the chemical structures were based on $^1H$, $^{13}C$, DEPT135, COSY, HMQC and HMBC NMR experiments. Chemical shifts (δ) are reported in parts per million (ppm). Signals are reported as an m (multiplet), s (singlet), d (doublet), brs (broad singlet) and coupling constants (J) are presented in hertz (Hz). Mass spectral data were obtained using a Finnigan Polaris Q GC/MS Benchtop Ion Trap mass spectrometer with a direct insertion probe.

PREPARATION EXAMPLES

Example 1

Intermediate 28-hydroxylup-20(29)-en-3β-yl acetate (Compound 3)

A mixture of betulin diacetate 6 (318 mg, 0.6 mmol) and methanolic KOH (66 ml, 0.6 mmol) in THF (20 ml) was stirred at rt over 17 h. The solution was acidified with aqueous HCl (3%) and extracted with ethyl acetate (3×30 ml). The combined ethereal extracts were washed with saturated solution of $Na_2CO_3$ (3×30 ml), and then with water (30 ml) and brine (30 ml). Dried with anhydrous $Na_2SO_4$, filtered, and concentrated under reduced pressure to give a white solid. Compound 3 (259 mg, 89%): IR (film) $\upsilon_{max}$ 3440, 3070, 1729, 1642, 1246, 978, 882 cm$^{-1}$; $^1$H NMR (CDCl$_3$, 300 MHz) δ 4.68 (s, 1H, H-29$_a$), 4.58 (s, 1H, H-29$_b$), 4.47 (dd, J=10.3 Hz, J=5.7 Hz, 1H, H-3α), 3.79 (d, J=10.7 Hz, 1H, H-28$_a$), 3.33 (d, J=10.7 Hz, 1H, H-28$_b$), 2.39 (dt, J=10.7, 5.9 Hz, 1H, H-19), 2.04 (s, 3H, OCOCH$_3$), 1.69 (s, 3H, 30-H), 1.02 (s, 3H), 0.97 (s, 3H), 0.85 (s, 6H), 0.84 (s, 3H); $^{13}$C NMR (CDCl$_3$, 75 MHz) δ 171.1 (OCOCH$_3$), 150.5 (C20), 109.7 (C29), 80.9 (C3), 60.5 (C28); EI-MS m/z (% rel. intensity): 484 (9) M$^+$, 203 (71), 189 (100), 187 (55); 107 (61), 105 (52), 95 (77), 91 (67), 81 (60), 79 (85)

Example 2

Intermediate

3β-hydroxylup-20(29)-en-28-yl acetate (Compound 4)

A mixture of betulin 1 (353 mg, 0.8 mmol), Ac$_2$O (4 ml) and imidazole (112 mg, 1.6 mmol) in CHCl$_3$ (60 ml) was heated under reflux for 2 h. After cooling, it was diluted with CHCl$_3$ (60 ml) and washed with ice cooled HCl (10%, 40 ml), water (30 ml) and brine (30 ml), and dried with Na$_2$SO$_4$. The solvent was evaporated and the residue purified by FCC with petroleum ether 40-60° C./ethyl acetate (4:1) and afforded compound 4 (323 mg, 84%) IR (film) $\upsilon_{max}$ 3471, 3070, 1734, 1642, 1244, 1102, 880 cm$^{-1}$; $^1$H NMR (CDCl$_3$, 300 MHz) δ 4.69 (s, 1H, H-29$_a$), 4.59 (s, 1H, H-29$_b$), 4.24 (d, J=10.9 Hz, 1H, H-28$_a$), 3.86 (d, J=10.9 Hz, 1H, H-28$_b$), 3.18 (dd, J=11.0 Hz, J=4.7 Hz, 1H, H-3α), 2.45 (dt, J=10.9, 5.8 Hz, 1H-19), 2.07 (s, 3H, OCOCH$_3$), 1.68 (s, 3H, H-30), 1.03 (s, 3H), 0.97 (s, 3H), 0.96 (s, 3H), 0.82 (s, 3H), 0.76 (s, 3H). $^{13}$C NMR (CDCl$_3$, 75 MHz) δ 171.6 (OCOCH$_3$), 150.2 (C20), 109.9 (C29), 78.9 (C3), 62.8 (C28); EI-MS m/z (% rel. intensity): 484 (12) M$^+$, 203 (54), 189 (100), 187 (71), 145 (49); 133 (67), 119 (62), 107 (49), 105 (69), 91 (56).

Example 3

Intermediate

Methyl 3β-hydroxylup-20(29)-en-28-oate (Compound 5)

To a solution of betulinic acid 2 (150 mg, 0.33 mmol) and anhydrous K$_2$CO$_3$ (115 mg, 0.83 mmol) in dry DMF (2 ml) was added methyl iodide (41 µl, 0.66 mmol). The mixture was stirred at room temperature for 1 h. After the reaction mixture was diluted in ethyl acetate (30 ml) and washed with water (3×20 ml) and brine (20 ml). The organic phase was dried with anhydrous Na$_2$SO$_4$, filtered, and concentrated under reduced pressure to give a yellowish solid. This solid was crystallized from methanol to yield compound 5 (129 mg, 83%) IR (film) $\upsilon_{max}$ 3320, 3070, 1720, 1643 cm$^{-1}$; $^1$H NMR (CDCl$_1$, 300 MHz) δ 4.71 (brs, 1H, H-29$_a$), 4.58 (brs, 1H, H-29$_b$), 3.67 (s, 3H, COOCH$_3$), 3.18 (dd, 1H, J=10.9 Hz, J=4.5 Hz, H-3α) 2.43 (m, 1H, H-19), 1.69 (s, 3H, H-30), 0.96 (s, 3H), 0.94 (3H), 0.92 (s, 3H), 0.82 (s, 3H), 0.75 (s, 3H). $^{13}$C NMR (CDCl$_3$, 75 MHz) δ 177.2 (C28), 149.7 (C20), 110.1 (C29), 80.6 (C3); EI-MS m/z (% rel. intensity): 471 (25) M$^+$, 286 (26), 253 (52), 247 (29), 203 (36), 192 (100), 189 (100), 175 (64), 119 (47), 105 (51).

Example 4

Intermediate

Lup-20(29)-en-3β,28-di-yl acetate (Compound 6)

A solution of betulin 1 (353 mg, 0.8 mmol), acetic anhydride (12 ml) and DMAP (100 mg, 0.82 mmol) was stirred for 12 h and then poured into ice-cooled aqueous HCl (10%, 50 ml). The mixture was extracted with ethyl acetate (3×30 ml), and the combined organic layers were washed with aqueous HCl (10%, 2×20 ml), water (30 ml) and brine (30 ml). Dried with anhydrous Na$_2$SO$_4$, filtered, and concentrated under reduced pressure to give a white solid. Compound 6 (373 mg, 89%): IR (film) $\upsilon_{max}$ 3073, 1735, 1642, 1241, 880 cm$^{-1}$; $^1$H NMR (CDCl$_3$, 300 MHz) δ 4.69 (brs, 1H, H-29$_a$) 4.59 (brs, 1H, H-29$_b$), 4.47 (dd, J=10.3 Hz, J=5.8 Hz, 1H, H-3α), 4.25 (d, J=11.0 Hz, 1H, H-28$_a$), 3.85 (d, J=11.0 Hz, 1H, H-28$_b$), 2.45 (dt, J=11.0, 5.8 Hz, 1H, H-19), 2.07 (s, 3H, OCOCH$_3$), 2.04 (s, 3H, OCOCH$_3$), 1.68 (s, 3H, H-30), 1.03 (s, 3H), 0.97 (s, 3H), 0.84 (s, 6H), 0.83 (s, 3H). $^{13}$C NMR (CDCl$_3$, 75 MHz) δ 171.6 (OCOCH$_3$), 171.0 (OCOCH$_3$), 150.1 (C20), 109.9 (C29), 80.9 (C3), 62.8 (C28); EI-MS m/z (% rel. intensity): 526 (5), M$^+$, 466 (72), 216 (46), 203 (47), 202 (44), 190 (53), 189 (100), 187 (68), 1.19 (47), 91 (51).

Example 5

Intermediates 30-methoxylup-20-(29)-en-3β,28-diol (Compound 7) and 30-bromolup-20(29)-en-3β,28-diol (Compound 8)

A solution of compound 6 (2.5 q, 4.75 mmol) in CCl$_4$ (100 ml) was treated with NBS (1.7 g, 9.55 mmol), stirred at reflux for 3 h and filtered through filter paper. The filtrate was evaporated, dissolved in MeOH (26 ml) and THF (12 ml) under Ar at 0° C. and treated with NaOH (1.2 ml, 4.8 mmol, 4N), held at room temperature for 29 h and poured onto ice with dilute HCl. The resulting solid was filtered off, washing with water and purified by FCC with petroleum ether 40-60° C./ethyl acetate (3:2) to afforded compound 7 (1.4 g, 64%): IR (film) $\upsilon_{max}$ 3347, 3073, 1645 cm$^{-1}$; $^1$H NMR (CDCl$_3$, 300 MHz) δ 4.92 (s, 1H, H-29$_a$), 4.91 (s, 1H, H-29$_b$), 3.86 (brs, 2H, H-30), 3.78 (d, J=10.5 Hz, 1H, H-28$_a$), 3.35 (s, 3H, OCH$_3$), 3.31 (d, J=10.5 Hz, 1H, H-28$_b$), 3.18 (dd, J=10.8 Hz, J=5.2 Hz, 1H, H-3α), 2.28 (dt, J=10.8 Hz, J=5.4 Hz, 1H, H-19) 1.02 (s, 3H), 0.98 (s, 3H), 0.97 (s, 3H), 0.82 (s, 3H), 0.76 (s, 3H). $^{13}$C NMR (CDCl$_3$, 75 MHz) δ 150.9 (C20), 109.0 (C29), 78.9 (C3) 74.8 (C30), 60.2 (C28), 58.3 (OCH$_3$). EI-MS m/z (% rel. intensity): 473 (25) M$^+$, 201 (93), 189 (86), 187 (100), 145 (75), 131 (66), 121 (71), 119 (73), 95 (66), 81

(69). Compound 8 (451 mg, 18%): IR (film) $\upsilon_{max}$ 3371, 3075, 1642 cm$^{-1}$; $^1$H NMR (CDCl$_3$, 300 MHz) δ 5.12 (s, 1H, H-29$_a$), 5.03 (s, 1H, H-29$_b$), 3.99 (s, 2H, H-30), 3.81 (d, J=10.8, 1H, H-28$_a$), 3.33 (d, J=10.8 Hz, 1H, H-28$_b$), 3.19 (dd, J=10.9 Hz, J=5.1 Hz, 1H, H-3α), 2.39 (dt, J=11.0 Hz, J=5.3 Hz, 1H, H-19) 1.03 (s, 3H), 0.99 (s, 3H), 0.97 (s, 3H), 0.82 (s, 3H), 0.76 (s, 3H). $^{13}$C NMR (CDCl$_3$, 75 MHz) δ 151.0 (C20), 109.8 (C29), 78.9 (C3), 60.3 (C28). EI-MS m/z (% rel. intensity): 522 (3) M$^+$, 121 (74), 119 (91), 107 (85), 105 (82), 93 (84), 91 (91), 81 (84), 79 (100), 67 (82).

Example 6

Intermediates

3β,28-dihydroxy-(20R)-lupan-29-al (Compound 9) and 3β,28-dihydroxy-(20.9)-lupan-29-al (Compound 10)

To a stirred solution of betulin 1 (868 mg, 1.96 mmol) in anhydrous CH$_2$Cl$_2$ (80 ml) at 0-5° C., m-CPBA (500 mg, 2.9 mmol) was added in one portion followed by stirring for 5 h. Then H$_2$SO$_4$ (4 ml, 2M) was added and the solution was stirred for 1 h. The resulting mixture was diluted with CH$_2$Cl$_2$ (100 ml), washed with saturated solution of Na$_2$CO$_3$ (3×30 ml), and then with water (30 ml) and brine (30 ml). Dried with anhydrous Na$_2$SO$_4$ to give a white solid. This solid was submitted to FCC with petroleum ether 40-60° C./ethyl acetate (3:2) and afforded compound 9 (354 mg, 39%): IR (film) $\upsilon_{max}$ 3393, 1714 cm$^{-1}$; $^1$H NMR (CDCl$_3$, 300 MHz) δ 9.86 (d, J=2.0 Hz, 1H, H-29), 3.77 (d, J=10.8 Hz, 1H, H-28$_a$), 3.26 (d, J=10.8 Hz, 1H, H-28$_b$), 3.20 (dd, J=10.9 Hz, J=5.1 Hz, 1H, H-3α) 2.60 (m, 1H, H-20), 1.10 (d, J=6.9 Hz, 3H, H-30), 1.03 (s, 3H), 0.98 (s, 3H), 0.95 (s, 3H), 0.84 (s, 3H), 0.77 (s, 3H). $^{13}$C NMR (CDCl$_3$, 75 MHz) δ 206.8 (CHO), 78.9 (C3), 60.2 (C28). EI-MS m/z (% rel. intensity): 458 (2) M$^+$, 369 (100), 207 (43), 192 (51), 189 (72), 161 (67), 133 (31), 121 (31), 107 (36), 95 (33). Compound 10 (179 mg, 20%): IR (film) $\upsilon_{max}$ 3340, 1716 cm$^{-1}$; $^1$H NMR (CDCl$_3$, 300 MHz) δ 9.62 (s, 1H, H-29), 3.80 (d, J=10.8 Hz, H-28$_a$), 3.33 (d, J=10.8 Hz, 1H, H-28$_b$), 3.20 (dd, J=10.9 Hz, J=5.1 Hz, 1H, H-3α), 2.65 (m, 1H, H-20), 1.06 (s, 3H), 1.04 (d, J=7.0 Hz, 3H, H-30), 0.98 (s, 6H), 0.84 (s, 3H), 0.77 (s, 3H). $^{13}$C NMR (CDCl$_3$, 75 MHz) δ 204.8 (CHO), 78.9 (C3), 60.2 (C28), EI-MS m/z (% rel. intensity): 458 (4) M$^+$, 369 (76), 207 (48), 190 (46), 1.89 (100), 161 (70), 119 (51), 105 (46), 95 (47), 91 (59).

Example 7

Intermediate 3-oxolup-20(29)-en-28-oic acid (Compound 11)

To a solution of betulin 1 (1 g, 2.26 mmol) in acetone (50 ml), cooled at 0° C., freshly prepared Jone's reagent was added dropwise. The resulting mixture was stirred for about 1.5 h at 0° C., quenched with methanol (25 ml), stirred for an additional 5 minutes, then water (40 ml) was added. The acetone was removed under vacuum and the aqueous residue was extracted with ethyl acetate (2×40 ml) and washed with water (30 ml) and brine (30 ml). Dried with Na$_2$SO$_4$, filtered, and concentrated under reduced pressure. The residue solid was submitted to FCC with petroleum ether 40-60° C./ethyl acetate (4:1) and afforded compound 11 (685 mg, 67%): IR (film) $\upsilon_{max}$ 3070, 1703, 1686, 1642 cm$^{-1}$; $^1$H NMR (CDCl$_3$, 300 MHz) δ 4.77 (brs, 1H, H-29$_a$), 4.64 (brs, 1H, H-29$_b$), 3.04 (dt, J=10.7 Hz, J=4.3 Hz, 1H, H-19), 1.72 (s, 3H, H-30), 1.09 (s, 3H), 1.04 (s, 3H), 1.02 (s, 3H), 0.99 (s, 3H), 0.95 (s, 3H). $^{13}$C NMR (CDCl$_3$, 75 MHz) δ 218.2 (C3), 182.2 (C28), 150.3 (C20), 109.7 (C29). EI-MS m/z (% rel. intensity): 454 (19) M$^+$, 408 (24), 393 (20), 248 (85), 189 (100), 175 (62), 133 (55), 119 (76), 105 (69), 79 (52).

Example 8

Intermediate 3-oxolup-1,20(29)-dien-28-oic acid (Compound 12)

A solution of compound 11 (400 mg, 0.88 mmol) and DDQ (597 mg, 2.64 mmol) in anhydrous dioxane (18 ml) Was heated under reflux and N$_2$ atmosphere for 15 h. After the reaction mixture was diluted in ethyl acetate (60 ml) and the insoluble matter was removed by filtration. The filtrate was washed with saturated solution of Na$_2$CO$_3$ (3×30 ml), and then with water (30 ml) and brine (30 ml). Dried with anhydrous Na$_2$SO$_4$, filtered, and concentrated under reduced pressure to give a yellowish solid. This solid was submitted to FCC with petroleum ether 40-60° C./ethyl acetate (4:1) to afford compound 12 (179 mg, 45%); IR (film) $\upsilon_{max}$ 3070, 1730, 1689, 1645 cm$^{-1}$; $^1$H NMR (CDCl$_3$, 400 MHz) δ 7.11 (d, J=10.3 Hz, 1H, H-1), 5.80 (d, J=10.3 Hz, 1H, H-2), 4.76 (s, 1H, H-29$_a$), 4.63 (s, 1H, H-29$_b$), 3.03 (m, 1H, H-19), 1.70 (s, 3H, H-30), 1.13 (s, 3H), 1.07 (s, 3H), 1.06 (s, 3H), 1.02 (s, 3H), 0.99 (s, 3H). $^{13}$C NMR (CDCl$_3$, 100 MHz) δ 205.9 (C3), 181.7 (C28), 160.1 (C1), 150.2 (C20), 125.1 (C2), 109.9 (C29). EI-MS m/z (% rel. intensity): 452 (17) M$^+$, 213 (100), 150 (39), 137 (34), 95 (31), 91 (42), 81 (36), 79 (41), 77 (29), 67 (34).

Example 9

Intermediate 2-hydroxy-3-oxolup-1,20(29)-dien-28-oic acid (Compound 13)

Compound 11 (363 mg, 0.8 mmol) was dissolved in a mixture of t-BuOK (3 g) in t-BuOH (32 ml). O$_2$ was constantly introduced into the vigorously stirred solution at 40° C. for 2 h. The reaction mixture was then poured into dilute HCl, extracted with ethyl acetate (2×40 ml) and washed with saturated solution of Na$_2$CO$_3$ (3×30 ml), water (30 ml) and brine (30 ml). Dried with Na$_2$SO$_4$, filtered, and concentrated under reduced pressure. The crude product was submitted to FCC with petroleum ether 40-60° C./ethyl acetate (3:2) and afforded compound 13 (2.73 mg, 7.3%): IR (film) $\upsilon_{max}$ 3389, 3073, 1730, 1698, 1669, 1645 cm$^{-1}$; $^1$H NMR (CDCl$_3$, 300 MHz) δ 6.45 (s, 1H, H-1), 4.75 (s, 1H, H-29$_b$), 4.64 (s, 1H, H-29$_b$), 3.02 (m, 1H, H-19), 1.70 (s, 3H, H-30), 1.20 (s, 3H), 1.13 (s, 3H), 1.10 (s, 3H), 1.00 (s, 3H), 0.98 (s, 3H). $^{13}$C NMR (CDCl$_3$, 75 MHz) δ 201.2 (C3), 182.4 (C28), 150.1 (C20), 143.9 (C2), 128.9 (C1), 109.9 (C29). EI-MS m/z (% rel. intensity): 469 (11) M$^+$, 321 (43), 213 (100), 189 (32), 150 (45), 136 (29), 91 (63), 80 (34), 75 (54), 69 (65).

Example 10

3β-hydroxy-lup-20(29)-en-28-yl-1H-imidazole-1-carboxylate (Compound 14) and Lup-20(29)-en-3β, 28-di-yl-(1H-imidazole-1-carboxylate) (Compound 17)

To a solution of betulin 1 (200 mg, 0.45 mmol) in anhydrous THF (8 ml), CDI (219 mg, 1.35 mmol) was added. After 7 h under magnetic stirring at reflux temperature and $N_2$ atmosphere, the reaction was completed as verified by TLC control. The reaction mixture was poured into water (30 ml) and extracted with diethyl ether (3×30 ml). The combined organic extract was then washed with water (30 ml), and brine (30 ml), dried with anhydrous $Na_2SO_4$, filtered and concentrated under reduced pressure to give a yellowish solid. This solid was submitted to FCC with petroleum ether 40-60° C./ethyl acetate (3:2) and afforded compound 14 (152 mg, 63%): mp (acetone) 202-204° C.; IR (film) $\upsilon_{max}$ 3570, 3078, 1751, 1645, 880 cm$^{-1}$; $^1$H NMR (CDCl$_3$, 300 MHz) δ 8.26 (s, 1H, H-2'), 7.46 (brs, 1H, H-5'), 7.13 (brs, 1H, H-4'), 4.72 (d, J=1.4 Hz, 1H, H-29$_a$), 4.67-4.63 (m, 2H, H-28$_a$ and H-29$_b$), 4.21 (d, J=10.7 Hz, 1H, H-28$_b$), 3.19 (dd, J=10.8 Hz, J=5.2 Hz, 1H, H-3α), 2.47 (dt, J=10.7 Hz, J=5.6 Hz, 1H, H-19), 1.70 (s, 3H, H-30), 1.06 (s, 3H), 1.01 (s, 3H), 0.97 (s, 3H), 0.83 (s, 3H), 0.76 (s, 3H); NMR (CDCl$_3$, 75 MHz) δ 149.5 (C20), 148.7 (OCO), 136.8 (C2'), 129.6 (C4'), 117.2 (C5'), 110.26 (C29), 78.9 (C3), 67.5 (C28); EI-MS m/z (% rel. intensity): 536 (12) M$^+$, 207 (36), 189 (39), 187 (54), 119 (44), 107 (34), 105 (34), 91 (46), 79 (38), 69 (100). And compound 17 (56 mg, 20%): mp (acetone/n-hexane) 161-163° C.; IR (film) $\upsilon_{max}$ 3070, 1757, 1642, 880 cm$^{-1}$; $^1$H NMR (CDCl$_3$, 300 MHz): δ 8.23 (s, 1H, H-2'), 8.22 (s, 1H, H-2"), 7.45 (s, 2H, H-5' and H-5"), 7.12 (s, 2H, H-4' and H-4"), 4.73-4.64 (m, 4H, H-3α, H-29$_a$, and H-29$_b$), 4.20 (d, J=10.7 Hz, 1H, 3H, 2.48 (m, 1H, H-19), 1.71 (s, 3H, H-30), 1.08 (s, 3H), 1.02 (s, 3H), 0.96 (s, 6H), 0.91 (s, 3H); $^{13}$C NMR (CDCl$_3$, 75 MHz): δ 149.4 (C20), 148.9 (OCO), 148.2 (OCO), 136.8 (C2'), 136.7 (C2"), 130.0 (C4'), 129.5 (C4"), 117.2 (C5'), 117.1 (C5"), 110.3 (C29), 86.8 (C3), 67.3 (C28); EI-MS m/z (% rel. intensity): 630 (2) M$^+$, 189 (67), 187 (73), 119 (72), 105 (80) 95 (65), 93 (56), 91 (84), 79 (60), 69 (100).

Example 11

3β-hydroxy-lup-20(29)-en-28-yl-2'-methyl-1H-imidazole-1-carboxylate (Compound 15) and Lup-20 (29)-en-3β,28-di-yl-(2'-methyl-1H-imidazole-1-carboxylate) (Compound 18)

To a solution of betulin 1 (200 mg, 0.45 mmol). in anhydrous THF (8 ml), CBMI (238 mg, 1.35 mmol) was added. After 9 h under magnetic stirring at reflux temperature and $N_2$ atmosphere, the reaction was completed as verified by TLC control. The reaction mixture was poured into water (30 ml) and extracted with diethyl ether (3×30 ml). The combined organic extract was then washed with water (30 ml), and brine (30 ml), dried with anhydrous $Na_2SO_4$, filtered and concentrated under reduced pressure to give a yellowish solid. This solid was submitted to FCC with petroleum ether 40-60° C./ethyl acetate (4:1) and afforded compound 15 (143 mg, 57%): mp (benzene) 163-165° C.; IR (film) $\upsilon_{max}$ 3313, 3073, 1758, 1642, 884 cm$^{-1}$; $^1$H NMR (CDCl$_3$, 300 MHz) δ 7.38 (d, J=1.7 Hz, 1H, H-5'), 6.91 (d, J=1.7 Hz, 1H, H-4'), 4.72 (brs, 1H, H-29$_a$), 4.62-4.59 (m, 2H, H-29$_b$ and H-28$_a$), 4.17 (d, J=10.9 Hz, 1H, H-28$_b$), 3.19 (dd, J=10.8 Hz, J=5.2 Hz, 1H, H-3α), 2.71 (s, 3H, CH$_3$-2'), 2.47 (m, 1H, H-19), 1.70 (s, 3H, H-30), 1.06 (s, 3H), 1.01 (s, 3H), 0.97 (s, 3H), 0.83 (s, 3H), 0.77 (s, 3H); $^{13}$C NMR (CDCl$_3$, 75 MHz) δ 149.6 (C20), 149.5 (OCO), 147.9 (C2'), 126.5 (C4'), 118.1 (C5'), 110.2 (C29), 78.8 (C3), 67.3 (C28); EI-MS m/z (% rel. intensity): 550 (10) M$^+$, 189 (26), 187 (26), 133 (25), 119 (37), 107 (28), 91 (30), 83 (27), 81 (27), 79 (26). And compound 18 (112 mg, 38%): mp (acetone/n-hexane) 127-129° C.; IR (film) $\upsilon_{max}$ 3070, 1753, 1645 cm$^{-1}$; $^1$H NMR (CDCl$_3$, 400 MHz): δ 7.36 (s, 1H, H-5'), 7.34 (s, 1H, H-5"), 6.86 (s, 1H, H-4"), 6.85 (s, 1H, H-4"), 4.73 (s, 1H, H-29$_a$), 4.67-4.58 (s, 3H, H-3α, H-28 H-29$_b$), 4.15 (d, J=10.8 Hz, 1H, H-280, 2.66 (s, 3H, CH$_3$-2"), 2.65 (s, 3H, CH$_3$-2"), 2.48 (m, 1H, H-19), 1.71 (s, 3H, H-30), 1.08 (s, 3H), 1.02 (s, 3H), 0.96 (s, 3H), 0.95 (s, 3H), 0.90 (s, 3H); $^{13}$C NMR (CDCl$_3$, 100 MHz): δ 150.0 (C20), 149.6 (OCO), 149.5 (OCO), 147.9 (C2' and C2"), 127.9 and 127.8 (C4', C4"), 118.0 (C5' and C5"), 110.3 (C29), 85.9 (C3), 66.7 (C28); EI-MS m/z (% rel. intensity): 658 (2) M$^+$, 127 (13), 119 (12), 105 (10), 95 (19); 93 (13), 91 (16), 83 (100), 81 (19), 79 (11).

Example 12

3β-hydroxy-lup-20(29)-en-28-yl-1H-triazole-1-carboxylate (Compound 16) and Lup-20(29)-en-3β,28-di-yl-(1H-triazole-1-carboxylate) (Compound 19)

To a solution of betulin 1 (200 mg, 0.45 mmol) in anhydrous THF (8 ml), CDT (295 mg, 1.8 mmol) was added. After 8 h under magnetic stirring at reflux temperature and $N_2$ atmosphere, the reaction was completed as verified by TLC control. The reaction mixture was poured into water (3.0 ml) and extracted with diethyl ether (3×30 ml). The combined organic extract was then washed with water (30 ml), and brine (30 ml), dried with anhydrous $Na_2SO_4$, filtered and concentrated under reduced pressure to give a yellowish solid. This solid was submitted to FCC with petroleum ether 40-60° C./ethyl acetate (3:2) and afforded compound 16 (175 mg, 72%): mp (acetone/n-hexane) 200-203° C.; IR (film) $\upsilon_{max}$ 3389, 3070, 1791, 1762, 1642, 882 cm$^{-1}$; $^1$H NMR (CDCl$_3$, 300 MHz) δ 8.83 (brs, 1H, H-5'), 8.09 (brs, 1H, H-3'), 4.74-4.72 (m, 2H, H-29$_a$ and H-28$_a$), 4.63 (brs, 1H, H-29$_b$), 4.30 (d, J=10.8 Hz, 1H, H-28$_b$), 3.19 (dd, J=10.8 Hz, J=5.2 Hz, 1H, H-3α), 2.49 (dt, J=10.7 Hz, J=6.0 Hz, 1H, H-19), 1.70 (s, 3H, H-30), 1.06 (s, 3H), 1.01 (s, 3H), 0.97 (s, 3H), 0.84 (s, 3H), 0.77 (s, 3H); $^{13}$C NMR (CDCl$_3$, 75 MHz) δ 153.6 (C3'), 149.5 (C20), 147.9 (OCO), 145.4 (C5'), 110.3 (C29), 78.9 (C3), 68.4 (C28); EI-MS m/z (% rel. intensity): 537 (4) M$^+$, 190 (74), 289 (100), 187 (89), 133 (72), 119 (98), 107 (75), 105 (82), 91 (93), 79 (89). And compound 19 (68 mg, 24%): mp (acetone/n-hexane) 157-159° C.; IR (film) $\upsilon_{max}$ 3070, 1787, 1763, 1642, 882 cm$^{-1}$; $^1$H NMR (CDCl$_3$, 400 MHz): δ 8.83 (brs, 1H, H-5'), 8.80 (brs, 1H, H-5") 8.09 (brs, 1H, H-3'), 8.08 (brs, 1H, H-3"), 4.82-4.73 (m, 3H, H-3α, H-28$_a$, H-29$_a$), 4.64 (brs, 1H, H-29$_b$), 4.30 (d, J=10.8 Hz, 1H, H-28$_b$), 2.50 (m, 1H, H-19), 1.72 (s, 3H, H-30), 1.09 (s, 3H), 1.02 (s, 3H), 1.00 (s, 3H), 0.98 (s, 3H), 0.92 (s, 3H); $^{13}$C NMR (CDCl$_3$, 100 MHz): δ 153.6 and 153.5 (C3', C3"), 149.4 (C20), 147.9 (OCO), 147.2 (OCO), 145.4 (C5'), 145.3 (C5"), 110.3 (C29), 87.7 (C3), 69.3 (C28); EI-MS m/z (% rel. intensity): 632 (4) M$^+$, 189 (86), 187 (62), 133 (67), 119 (79), 107 (60), 105 (83), 95 (67), 93 (74), 91 (100).

Example 13

28-hydroxy-lup-20(29)-en-3β-yl-1H-imidazole-1-carboxylate (Compound 20)

A solution of betulin 1 (200 mg, 0.45 mmol) and CDI (365 mg, 2.25 mmol) in anhydrous THF (8 ml) was refluxed for 9 h to obtained compound 17. Silica gel (200 mg) was added and this mixture was stirred at room temperature for 18 h. The solid was filtered off and the filtrate was poured into water (30 ml) and extracted with diethyl ether (3×30 ml). The organic phase was then washed with water (30 ml), and brine (30 ml), dried with $Na_2SO_4$, filtered, and evaporated to dryness. The crude product was purified by FCC eluting with petroleum ether 40-60° C./ethyl acetate (3:2) to yield compound 20 (166 mg, 68%): mp (acetone/n-hexane) 198-199° C.; IR (film) $\upsilon_{max}$ 3327, 3070, 1758, 1645, 882 cm$^{-1}$; NMR (CDCl$_3$, 300 MHz) 5) 8.29 (s, 1H, H-2'), 7.47 (s, 1H, H-5'), 7.15 (s, 1H, H-4'), 4.73-4.69 (m, 2H, H-3α and H-29$_a$), 4.59 (m, 1H, H-29$_b$), 3.80 (d, J=10.7 Hz, 1H, H-28$_a$), 3.34 (d, J=10.7 Hz, 1H, H-28$_b$), 2.40 (dt, J=10.7 Hz, J=5.7 Hz, 1H, H-19), 1.69 (s, 3H, H-30), 1.04 (s, 3H), 0.99 (s, 3H), 0.96 (s, 3H), 0.95 (s, 3H), 0.89 (s, 3H); $^{13}$C NMR (CDCl$_3$, 75 MHz) δ 150.4 (C20), 147.9 (OCO), 136.6 (C2'), 128.9 (C4'), 117.4 (C5'), 109.7 (C29), 87.1 (C3), 60.4 (C28); EI-MS m/z (% rel. intensity): 536 (6) M$^+$, 203 (37), 189 (35), 119 (41), 105 (37), 95 (35), 91 (30), 81 (29), 79 (32), 69 (100).

Example 14

28-hydroxy-lup-20(29)-en-3β-yl-1H-triazole-1-carboxylate (Compound 21)

A solution of betulin 1 (200 mg, 0.45 mmol) and CDT (443 mg, 2.7 mmol) in anhydrous THF (8 ml) was refluxed for 10 h to obtained compound 19. Silica gel (200 mg) was added and this mixture was stirred at room temperature for 15 h. The solid was filtered off and the filtrate was poured into water (30 ml) and extracted with diethyl ether (3×30 ml). The organic phase was then washed with water (30 ml), and brine (30 ml), dried with Na$_2$SO$_4$, filtered, and evaporated to dryness. The crude product was purified by FCC eluting with petroleum ether 40-60° C./ethyl acetate (3:2) to yield compound 21 (152 mg, 63%): mp (acetone/n-hexane) 221-224° C.; IR (film) $\upsilon_{max}$ 3406, 3070, 1764, 1642, 886 cm$^{-1}$; $^1$H NMR (CDCl$_3$, 300 MHz) δ 8.79 (s, 1H, H-5'), 8.08 (s, 1H, H-3'), 4.79 (dd, J=9.1, 7.5 Hz, 1H, H-3α), 4.69 (brs, 1H, H-29$_a$), 4.59 (brs, 1H, H-29$_b$), 3.80 (d, J=10.8 Hz, 1H, H-28$_a$), 3.34 (d, J=10.8 Hz, 1H, H-28$_b$), 2.40 (dt, J=10.5 Hz, J=5.8 Hz, 1H, H-19), 1.69 (s, 3H, H-30), 1.04 (s, 3H), 0.99 (s, 6H), 0.98 (s, 3H), 0.90 (s, 3H); $^{13}$C NMR (CDCl$_3$, 75 MHz) δ 153.4 (C3'), 150.4 (C20), 147.2 (OCO), 145.3 (C5'), 109.7 (C29), 87.8 (C3), 60.4 (C28); EI-MS m/z (% rel. intensity): 537 (6.) M$^+$, 119 (49), 107 (46), 105 (60), 93 (55), 91 (100), 81 (46), 79 (53), 77 (51), 70 (38).

Example 15

3β-acetoxy-lup-20(29)-en-28-yl-1H-imidazole-1-carboxylate (Compound 22)

The method followed that described for compound 14 but using compound 3 (242 mg, 0.5 mmol) and CDI (162 mg, mmol) in anhydrous THF (10 ml) at reflux for 5 h. The resulting white solid was purified by FCC using petroleum ether 40-60° C./ethyl acetate (4:1) to afford compound 22 (247 mg, 85%): mp (acetone/n-hexane) 101-103° C.; IR (film). $\upsilon_{max}$ 3073, 1760, 1730, 1642, 1240, 882 cm$^{-1}$; $^1$H NMR (CDCl$_3$, 300 MHz) δ 8.22 (s, 1H, H-2'), 7.45 (s, 1H, H-5'), 7.12 (s, 1H, H-4'), 4.72 (brs, 1H, H-29$_a$), 4.67-4.63 (m, 2H, H-28$_a$ and R-290, 4.47 (dd, J=10.2 Hz, J=5.8 Hz, 1H, H-3α), 4.20 (d, J=10.6 Hz, 1H, H-28$_b$), 2.48 (m, 1H, H-19), 2.05 (s, 3H, OCOCH$_3$), 1.71 (s, 3H, H-30), 1.06 (s, 3H), 1.00 (s, 3H), 0.86 (s, 3H), 0.85 (s, 3H), 0.84 (s, 3H); $^{13}$C NMR (CDCl$_3$, 75 MHz) δ 170.9 (OCOCH$_3$), 149.5 (C20), 148.8 (OCO), 136.8 (C2'), 129.9 (C4'), 117.2 (C5'), 110.3 (C29), 80.8 (C3), 67.4 (C28); EI-MS m/z (% rel. intensity): 578 (19) M$^+$, 189 (24), 187 (26), 133 (20), 119 (35), 105 (36), 93 (19), 91 (42), 79 (26), 69 (100).

Example 16

3β-acetoxy-lup-20(29)-en-28-yl-2'-methyl-1H-imidazole-1-carboxylate (Compound 23)

The method followed that described for compound 15 but using compound 3 (242 mg, 0.5 mmol) and CBMI (0.176 mg, 1 mmol) in anhydrous THF (10 ml) at reflux for 7 h. The resulting white solid was purified by FCC using petroleum ether 40-60° C./ethyl acetate (4:2) to afford compound 23 (253 mg, 86%): mp (acetone/n-hexane) 99-102° C.; IR (film) $\upsilon_{max}$ 3073, 1757, 1731, 1642, 1245, 882 cm$^{-1}$; $^1$H NMR (CDCl$_3$, 300 MHz) δ 7.38 (d, J=1.8 Hz, 1H, H-5'), 6.90 (d, J=1.8 Hz, 1H, H-4'), 4.72 (brs, 1H, H-29), 4.62-4.58 (m, 2H, H-28, and H-29$_b$), 4.47 (dd, J=10.2 Hz, J=5.8 Hz, 1H, H-3α), 4.16 (d, J=10.8 Hz, 1H, H-28$_b$), 2.70 (s, 3H, CH$_3$-2'), 2.48 (dt, J=10.7 Hz, J=5.7 Hz, 1H, H-19), 2.05 (s, 3H, OCOCH$_3$), 1.71 (s, 3H, H-30), 1.06 (s, 3H), 0.99 (s, 3H), 0.86 (s, 3H), 0.85 (s, 3H), 0.84 (s, 3H); $^{13}$C NMR (CDCl$_3$, 75 MHz) δ 170.9 (OCOCH$_3$), 149.7 (C20), 149.5 (OCO), 147.9 (C2'), 127.1 (C4'), 118.1 (C5'), 110.2 (C29), 80.8 (C3), 67.0 (C28); EI-MS m/z (% rel. intensity): 592 (14) M$^+$, 189 (20), 187 (16), 145 (15), 119 (22), 107 (19), 105 (25), 91 (28), 83 (100), 79 (16).

Example 17

3β-acetoxy-lup-20(29)-en-28-yl-1H-triazole-1-carboxylate (Compound 24)

The method followed that described for compound 16 but using compound 3 (242 mg, 0.5 mmol) and CDT (246 mg, 1.5 mmol) in anhydrous THF (10 ml) at reflux for 6 h. The resulting white solid was purified by FCC using petroleum ether 40-60° C./ethyl acetate (4:2) to afford compound 24 (213 mg, 74%): mp (acetone/n-hexane) 111-114° C.; IR (film) $\upsilon_{max}$ 3070, 1795, 1770, 1729, 1642, 1247, 882 cm$^{-1}$; $^1$H NMR (CDCl$_3$, 300 MHz) δ 8.82 (s, 1H, H-5'), 8.09 (s, 1H, H-3'), 4.75-4.72 (m, 2H, H-28, and H-29$_a$), 4.63 (brs, 1H, H-29$_b$), 4.47 (dd, J=10.2 Hz, J=5.8 Hz, 1H, H-3α), 4.30 (d, J=10.7 Hz, 1H, H-28$_b$), 2.49 (dt, J=10.6 Hz, J=6.0 Hz, 1H, H-19), 2.05 (s, 3H, OCOCH$_3$), 1.71 (s, 3H, H-30), 1.06 (s, 3H), 1.00 (s, 3H), 0.86 (s, 3H), 0.85 (s, 3H), 0.84 (s, 3H); $^{13}$C NMR (CDCl$_3$, 75 MHz) δ 171.0 (OCOCH$_3$), 153.6 (C3'), 149.5 (C20), 147.9 (OCO), 145.4 (C5'), 110.3 (C29), 80.8 (C3), 68.4 (C28); EI-MS m/z (% rel. intensity): 579 (6) M$^+$, 202 (58), 189 (88), 187 (78), 145 (59), 119 (78), 107 (62), 105 (77), 91 (100), 79 (58).

Example 18

28-acetoxy-lup-20(29)-en-3β-yl-1H-imidazole-1-carboxylate (Compound 25)

The method followed that described for compound 14 but using compound 4 (242 mg, 0.5 mmol) and CDI (162 mg, 1 mmol) in anhydrous THF (10 ml) at reflux for 7 h. The resulting white solid was purified by FCC using petroleum ether 40-60° C./ethyl acetate (4:1) to afford compound 25 (235 mg, 81%): mp (acetone/n-hexane) 194-195° C.; IR (film) $\upsilon_{max}$ 3070, 1756, 1733, 1642, 1239, 882 cm$^{-1}$; NMR (CDCl$_3$, 400 MHz) δ 8.12 (s, 1H, H-2'), 7.41 (s, 1H, H-5'), 7.07 (s, 1H, H-4'), 4.70-4.66 (m, 2H, H-3α and H-29$_a$) 4.60 (s, 1H, H-29$_b$), 4.26 (d, J=11.0 Hz, 1H, H-28$_a$), 3.85 (d, J=11.0 Hz, 1H, H-28$_b$), 2.45 (dt, J=10.8 Hz, J=5.9 Hz, 1H, H-19), 2.07 (s, 3H, OCOCH$_3$), 1.69 (s, 3H, H-30), 1.05 (s, 3H), 0.99 (s, 3H), 0.95 (s, 6H), 0.89 (s, 3H); $^{13}$C NMR (CDCl$_3$, 100 MHz) δ 171.6 (OCOCH$_3$), 150.0 (C20), 14.8.5 (OCO), 137.0

(C2'), 130.5 (C4'), 117.0 (C5'), 109.9 (C29), 86.3 (C3), 62.8 (C28); EI-MS m/z (% rel. intensity): 578 (5), M+, 189 (64), 187 (56), 145 (44), 133 (43), 119 (51), 105 (66), 95 (50), 91 (71), 69 (100).

Example 19

28-acetoxy-lup-20(29)-en-3β-yl-2'-methyl-1H-imidazole-1-carboxylate (Compound 26)

The method followed that described for compound 15 but using compound 4 (242 mg, 0.5 mmol) and CBMI (176 mg, 1 mmol) in anhydrous THF (10 ml) at reflux for 9 h. The resulting white solid was purified by FCC using petroleum ether 40-60° C./ethyl acetate (4:1) to afford compound 26 (243 mg, 82%): mp (acetone/n-hexane) 173-175° C.; IR (film) $\upsilon_{max}$ 3070, 1740, 1642, 882 cm$^{-1}$; $^1$H NMR (CDCl$_3$, 300 MHz) δ 7.36 (d, J=1.5 Hz, 1H, H-5'), 6.90 (d, J=1.5 Hz, 1H, H-4'), 4.69-4.64 (m, 2H, H-3α and H-29$_a$), 4.60 (brs, 1H, H-29$_b$), 4.26 (d, J=11.0 Hz, 1H, H-28$_a$), 3.85 (d, J=11.0 Hz, 1H, H-28$_b$), 2.69 (s, 3H, CH$_3$-2'), 2.45 (dt, J=10.7 Hz, J=5.7 Hz, 1H, H-19), 2.08 (s, 3H, OCOCH$_3$), 1.69 (s, 3H, H-30), 1.05 (s, 3H), 0.99 (s, 3H), 0.96 (s, 3H), 0.95 (s, 3H), 0.89 (s, 3H); $^{13}$C NMR (CDCl$_3$, 75 MHz) δ 171.6 (O$\underline{C}$OCH$_3$), 150.0 (C20), 149.1 (OCO), 147.9 (C2'), 126.8 (C4'), 118.1 (C5'), 109.9 (C29), 86.4 (C3), 62.7 (C28); EI-MS m/z (% rel. intensity): 592 (6) M, 467 (100), 407 (58), 107 (45), 105 (56), 95 (70), 91 (52), 83 (40), 81 (61), 67 (53).

Example 20

28-acetoxy-lup-20(29)-en-3β-yl-1H-triazole-1-carboxylate (Compound 27)

The method followed that described for compound 16 but using compound 4 (242 mg, 0.5 mmol) and CDT (246 mg, 1.5 mmol) in anhydrous THF (10 ml) at reflux for 8 h. The resulting white solid was purified by FCC using petroleum ether 40-60° C./ethyl acetate (4:1) to afford compound 27 (256 mg, 88%): mp (acetone/n-hexane) 221-224° C.; IR (film) $\upsilon_{max}$ 3070, 1787, 1766, 1733 cm$^{-1}$; $^1$H NMR (CDCl$_3$, 400 MHz) δ 8.79 (s, 1H, H-5'), 8.08 (s, 1H, H-3'), 4.79 (dd, J=9.0 Hz, J=7.5 Hz, 1H, H-3α), 4.69 (brs, 1H, H-29$_a$), 4.60 (brs, 1H, H-29$_b$), 4.26 (d, J=10.9 Hz, 1H, H-28$_a$), 3.85 (d, J=10.9 Hz, 1H, H-28$_b$), 2.45 (dt, J=10.9 Hz, J=5.8 Hz, 1H, H-19), 2.07 (s, 3H, OCOCH$_3$), 1.69 (s, 3H, H-30), 1.05 (s, 3H), 0.99 (s, 3H), 0.98 (s, 3H), 0.97 (s, 3H), 0.90 (s, 3H); $^{13}$C NMR (CDCl$_3$, 100 MHz) δ 171.6 (O$\underline{C}$OCH$_3$), 153.5 (C3'), 150.1 (C20), 147.3 (OCO), 145.3 (C5'), 109.9 (C29), 87.9 (C3), 62.8 (C28); EI-MS m/z (% rel. intensity): 579 (4) M+, 203 (51), 189 (84), 187 (69), 159 (47), 119 (56), 107 (57), 105 (75), 91 (100), 79 (54).

Example 21

3β-(1H-imidazole-1-carbonyloxy)-lup-20(29)-en-28-oic acid (Compound 28) and 28-(1H-imidazole-1-yl)-28-oxo-lup-20(29)-en-3β-yl-1H-imidazole-1-carboxylate (Compound 30)

The method followed that described for compound 14 but using betulinic acid 2 (297 mg, 0.65 mmol) and CDT (527 mg, 3.25 mmol) in anhydrous THF (12 ml) at reflux for 7 h. The resulting yellowish solid was purified by FCC using petroleum ether 40-60° C./ethyl acetate (2:3) to afford compound 28 (249 mg, 70%): mp (acetone/n-hexane) 228-230° C.; IR (film) $\upsilon_{max}$ 3070, 1762, 1699, 1642 cm$^{-1}$; $^1$H NMR (CDCl$_3$, 300 MHz) δ 8.21 (s, 1H, H-2'), 7.43 (s, 1H, H-5'), 7.12 (s, 1H, H-4'), 4.75 (brs, 1H, H-29$_a$), 4.69 (dd, J=10.1 Hz, J=6.2 Hz, 1H, H-3α), 4.62 (brs, 1H, H-29$_b$), 3.04 (dt, J=10.7 Hz, J=4.1 Hz, 1H, H-19), 1.70 (s, 3H, H-30), 0.99 (s, 3H), 0.96-0.95 (m, 9H), 0.89 (s, 3H); $^{13}$C NMR (CDCl$_3$, 75 MHz) δ 181.5 (C28), 150.5 (C20), 148.3 (OCO), 136.9 (C2'), 129.8 (C4'), 117.2 (C5'), 109.7 (C29), 86.6 (C3); EI-MS m/z (% rel. intensity): 550 (4) M+, 203 (41), 189 (50), 187 (40), 175 (42), 159 (37), 119 (47), 91 (41), 79 (36), 69 (100). And compound 30 (88 mg, 23%): mp (acetone/n-hexane) 150-151° C.; IR (film) $\upsilon_{max}$ 3073, 1757, 1722, 1642 cm$^{-1}$; $^1$H NMR (CDCl$_3$, 400 MHz) δ 8.28 (s, 1H, H2'), 8.13 (s, 1H, H2''), 7.53 (s, 1H, H-5'), 7.41 (s, 1H, H-5''), 7.07 (s, 1H, H-4'') 7.05 (s, 1H, H-4'), 4.78 (brs, 1H, H-29$_a$), 4.69-4.66 (m, 2H, H-3α, H-29$_b$), 2.97 (dt, J=10.9 Hz, J=4.5 Hz, 1H, H-19), 1.72 (s, 3H, H-30), 1.01 (s, 3H), 0.95 (s, 9H), 0.91 (s, 3H); $^{13}$C NMR (CDCl$_3$, 100 MHz) δ 172.9 (C28) 149.7 (C20), 148.5 (OCO), 137.3 (C2'), 137.0 (C2''), 130.5 (C4''), 129.6 (C4'), 117.4 (C5'), 117.0 (C5''), 110.2 (C29), 86.3 (C3); EI-MS m/z (% rel. intensity): 600 (4) M+, 393 (33), 203 (22), 189 (31), 107 (27), 105 (27), 95 (38), 91 (28), 81 (24), 69 (100).

Example 22

3β-(1H-imidazole-2'-methyl-1-carbonyloxy)-lup-20(29)-en-28-oic acid (Compound 29) and 28-(2'-methyl-1H-imidazole-1-yl)-28-oxo-lup-20(29)-en-3β-yl-2'-methyl-1H-imidazole-1-carboxylate (Compound 31)

The method followed that described for compound 15 but using betulinic acid 2 (297 mg, 0.65 mmol) and CBMI (573 mg, 3.25 mmol) in anhydrous THF (12 ml) at reflux for 8 h. The resulting yellowish solid was purified by FCC using petroleum ether 40-60° C./ethyl acetate (3:2) to afford compound 29 (283 mg, 77%): mp (acetone/n-hexane) 170-174° C.; IR (film) $\upsilon_{max}$ 3070, 1756, 1703, 1642, 883 cm$^{-1}$; $^1$H NMR (CDCl$_3$, 300 MHz) δ 7.35 (d, J=1.6 Hz, 1H, H-5'), 6.88 (d, J=1.6 Hz, 1H, H-4'), 4.75 (brs, 1H, H-29$_a$), 4.68-4.61 (m, 2H, H-3α and H-29$_b$), 3.05 (dt, J=10.7 Hz, J=4.3 Hz, 1H, H-19), 2.67 (s, 3H, CH$_3$-2'), 1.70 (s, 3H, H-30), 0.99 (s, 3H), 0.96 (s, 3H), 0.95 (s, 3H), 0.94 (s, 3H), 0.89 (s, 3H); $^{13}$C NMR (CDCl$_3$, 75 MHz) δ 180.6 (C28), 150.6 (C20), 149.3 (OCO), 147.9 (C2'), 127.3 (C4'), 118.0 (C5''), 109.6 (C29), 86.2 (C3); EI-MS m/z (% rel. intensity) 564 (10) M+, 439 (100), 393 (61), 203 (58), 123 (50), 121 (50), 109 (57), 95 (74), 83 (66), 81 (97). And compound 31 (90 mg, 22%): mp (ethyl acetate/n-hexane) 164-166° C.; IR (film) $\upsilon_{max}$ 3070, 1752, 1722, 1642 cm$^{-1}$; $^1$H NMR (CDCl$_3$, 400 MHz) δ 7.39 (brs, 1H, H-5'), 7.34 (brs, 1H, H-5''), 6.86 (brs, 2H, H-4' and H4''), 4.79 (brs, 1H, H-29$_a$), 4.66-4.62 (m, 1H, H-3α, H-29$_b$), 3.06 (dt, J=11.0 Hz, J=4.3 Hz, 1H, H-19), 2.65 (s, 3H, CH$_3$-2'), 2.63 (s, 3H, CH$_3$-2''), 1.73 (s, 3H, H-30), 1.01 (s, 3H), 0.96 (s, 3H), 0.94 (s, 6H), 0.89 (s, 3H); $^{13}$C NMR (CDCl$_3$, 100 MHz) δ 175.2 (C28), 150.0 (C20), 149.5 (OCO), 148.9 and 147.9 (C2', C2''), 127.7 and 127.1 (C4', C4''), 118.0 (C5' and C5''), 110.1 (C29), 85.9 (C3); EI-MS m/z (% rel. intensity): 628 (2) M+, 519 (18), 127 (30), 119 (17), 105 (20), 95 (22), 93 (18), 91 (19), 83 (100), 81 (24).

Example 23

28-(1H-triazole-1-yl)-28-oxo-lup-20(29)-en-3β-yl-1H-triazole-1-carboxylate (Compound 32)

The method followed that described for compound 16 but using betulinic acid 2 (297 mg, 0.65 mmol) and CDT (640 mg, 3.9 mmol) in anhydrous THF (12 ml) at reflux for 7 h. The resulting yellowish solid was purified by FCC using petroleum ether 40-60° C./ethyl acetate (3:2) to afford compound 32 (322 mg, 82%): mp (acetone/n-hexane) 253-256° C.; IR (film) $v_{max}$ 3070, 1787, 1762, 1734, 1642 cm$^{-1}$; $^1$H NMR (CDCl$_3$, 300 MHz) δ 8.93 (s, 1H, H-5'), 8.79 (s, 1H, H-5''), 8.07 (s, 1H, H-3''), 8.00 (s, 1H, H-3'), 4.81-4.78 (m, 2H, H-3α and H-29), 4.66 (brs, 1H, H-29$_b$), 2.96 (m, 1H, H-19), 1.73 (s, 3H, H-30), 1.02 (s, 3H), 0.99 (s, 3H), 0.97 (s, 3H), 0.95 (s, 3H), 0.92 (s, 3H); $^{13}$C NMR (CDCl$_3$, 75 MHz) δ 173.4 (C28), 153.6 (C3''), 152.1 (C3'), 149.9 (C20), 147.3 (OCO), 145.3 (C5''), 145.1 (C5'), 110.1 (C29), 87.8 (C3); EI-MS m/z (% rel. intensity): 602 (10) M', 202 (70), 190 (86), 189 (93), 188 (100), 187 (65), 173 (72), 105 (62), 91 (85), 70 (84).

Example 24

Methyl 3β-(1H-imidazole-1-carbonyloxy)-lup-20(29)-en-28-oate (Compound 33)

The method followed that described for compound 14 but using compound 5 (100 mg, 0.2 mmol) and CDI (65 mg, 0.4 mmol) in anhydrous THF (4 ml), at reflux for 6 h. The crude product was purified by FCC eluting with petroleum ether 40-60° C./ethyl acetate (3:2) to yield compound 33 (105 mg, 88%): mp (acetone/n-hexane) 220-224° C.; IR (film) $v_{max}$ 3070, 1758, 1725, 1642, 1240 cm$^{-1}$; $^1$H NMR (CDCl$_3$, 300 MHz) δ 8.24 (s, 1H, H2'), 7.45 (s, 1H, H-5'), 7.13 (s, 1H, H-4'), 4.74-4.67 (m, 2H, H-3α, H-29$_a$), 4.61 (brs, 1H, H-29$_b$), 3.67 (s, 3H, COOCH$_3$), 3.00 (dt, J=10.3 Hz, J=3.7 Hz, 1H, H-19), 1.69 (s, 3H, H-30), 0.97 (s, 3H), 0.95 (s, 6H), 0.93 (s, 3H), 0.89 (s, 3H); $^{13}$C NMR (CDCl$_3$, 75 MHz) δ 176.6 (C28), 150.5 (C20), 148.1 (OCO), 136.6 (C2'), 129.3 (C4'), 117.2 (C5'), 109.6 (C29), 86.9 (C3); EI-MS m/z (% rel. intensity): 564 (4) M$^+$, 203 (35), 190 (28), 189 (71), 187 (38), 175 (35), 119 (43), 105(33), 91 (37), 79 (33) 69 (100).

Example 25

Methyl 3β-(2'-methyl-1H-imidazole-1-carbonyloxy)-lup-20(29)-en-28-oate (Compound 34)

The method followed that described for compound 15 but using compound 5 (100 mg, 0.2 mmol) and CBMI (70 mg, 0.4 mmol) in anhydrous THF (4 ml), at reflux for 9 h. The crude product was purified by FCC eluting with petroleum ether 40-60° C./ethyl acetate 3:2) to yield compound 34 (115 mg, 93%): mp (acetone/n-hexane) 205-207° C.; IR (film) $v_{max}$ 3073, 1752, 1728, 1642 cm$^{-1}$; $^1$H NMR (CDCl$_3$, 400 MHz) δ 7.34 (brs, 1H, H-5'), 6.85 (brs, 1H, H-4'), 4.74 (s, 1H, H-29$_3$), 4.65 (dd, J=11.2 Hz, J=5.1 Hz, 1H, H-3α), 4.61 (s, 1H, H-29$_b$), 3.67 (s, 3H, COOCH$_3$), 3.00 (dt, J=10.4 Hz, J=3.8 Hz, 1H, H-19), 2.65 (s, 3H, CH$_3$-2'), 1.69 (s, 3H, H-30), 0.98 (s, 3H), 0.95 (s, 3H), 0.94 (s, 3H), 0.93 (s, 3H), 0.88 (s, 3H); $^{13}$C NMR (CDCl$_3$, 100 MHz) δ 176.6 (C28), 150.5 (C20), 149.5 (OCO), 147.9 (C2'), 127.7 (C4'), 118.0 (C5'), 109.7 (C29), 86.0 (C3); EI-MS m/z (% rel. intensity): 578 (13) De, 393 (100), 189 (68), 119 (56), 105 (64), 95 (71), 91 (75), 83 (87), 81 (70), 79 (52).

Example 26

3β-hydroxy-30-methoxylup-20(29)-en-28-yl-1H-imidazole-1-carboxylate (Compound 35) and 30-methoxylup-20(29)-en-3β,28-di-yl-(1H-imidazole-1-carboxylate) (Compound 38)

The method followed that described for compound 14 but using compound 7 (213 mg, 0.45 mmol) and CDI (219 mg, 1.35 mmol) in anhydrous THF (8 ml), at reflux for 8 h. The resulting white solid was purified by FCC eluting with petroleum ether 40-60° C./ethyl acetate (1:1) to afford compound 35 (174 mg, 68%): rap (acetone/n-hexane) 136-138° C.; IR (film) $v_{max}$ 3406, 3078, 1760, 1645, 1239 cm$^{-1}$; $^1$H NMR (CDCl$_3$, 300 MHz) δ 8.23 (s, 1H, H-2'), 7.47 (s, 1H, H-5'), 7.13 (s, 1H, H-4'), 4.98 (s, 1H, H-29$_a$), 4.95 (s, 1H, H-29$_b$), 4.65 (d, J=10.8 Hz, 1H, H-28$_a$), 4.21 (d, J=10.8 Hz, 1H, H-28$_b$), 3.89 (s, 2H, H-30), 3.38 (s, 3H, OCH$_3$), 3.20 (dd, J=10.8 Hz, J=5.1 Hz, 1H, H-3α), 2.39 (dt, J=11.0 Hz, J=5.3 Hz, 1H, H-19), 1.07 (s, 3H), 1.02 (s, 3H), 0.98 (s, 3H), 0.84 (s, 3 h), 0.78 (s, 38); $^{13}$C NMR (CDCl$_3$, 75 MHz) δ 150.3 (C20), 148.8 (OCO), 136.8 (C2'), 129.9 (C4'), 117.2 (C5'), 109.7 (C29), 78.8 (C3), 74.9 (C30), 67.2 (C28), 58.3 (OCH$_3$); EI-MS m/z (% rel. intensity): 566 (7) M', 187 (30), 119 (34), 105 (32), 93 (32), 91 (46), 81 (33), 79 (39), 69 (100), 67 (29). And compound 38 (83 mg, 28%): mp (acetone/n-hexane) 174-176° C.; IR (film) $v_{max}$ 3078, 1757, 1645, 1239 cm$^{-1}$; $^1$H NMR (CDCl$_3$, 400 MHz) δ 8.15 (s, 1H, H-2'), 8.13 (s, 1H, H-2''), 7.43 (s, 1H, H-5'), 7.41 (s, 1H, H-5''), 7.08 (s, 1H, H-4'), 7.07 (s, 1H, H-4''), 4.98 (s, 1H, H-29$_a$), 4.95 (s, 1H, H-29$_b$), 4.70-4.62 (m, 2H, H-3α, H-28$_a$), 4.18 (d, J=10.7 Hz, 1H, H-28$_b$), 3.89 (s, 2H, H-30), 3.37 (s, 3H, OCH$_3$), 2.40 (dt, J=11.0 Hz, J=5.3 Hz, 18, H-19), 1.09 (s, 3H), 1.03 (s, 3H), 0.96 (s, 6H), 0.91 (s, 3H); $^{13}$C NMR (CDCl$_3$, 100 MHz) δ 150.4 (C20), 149.1 (OCO), 148.5 (OCO), 137.0 (C2', C2''), 130.7 and 130.6 (C4', C4''), 117.0 (C5', C5''), 109.9 (C29), 86.2 (C3), 75.1 (C30), 66.9 (C28), 58.4 (OCH$_3$); EI-MS m/z (% rel. intensity): 660 (11) M$^+$, 199 (23), 189 (25), 187 (30), 145 (28), 143 (20), 119 (22), 105 (21), 91 (34), 69 (100).

Example 27

3β-hydroxy-30-methoxylup-20(29)-en-28-yl-2'-methyl-1H-imidazole-1-carboxylate (Compound 36) and 30-methoxylup-20(29)-en-3β,28-di-yl-(2'-methyl-1H-imidazole-1-carboxylate) (Compound 39)

The method followed that described for compound 14 but using compound 7 (213 mg, 0.45 mmol) and CBMI (238 mg, 1.35 mmol) in anhydrous THF (8 ml), at reflux for 7 h. The resulting white solid was purified by FCC eluting with petroleum ether 40-60° C./ethyl acetate (2:1) to afford compound 36 (193 mg, 74%): mp (acetone/n-hexane) 109-112° C.; IR (film) $v_{max}$ 3389, 3070, 1759, 1645 cm$^{-1}$; $^1$H NMR (CDCl$_3$, 300 MHz) δ 7.37 (d, J=1.7 Hz, 1H, H-5'), 6.88 (d, J=1.7 Hz, 1H, H-4'), 4.96 (brs, 1H, H-29$_a$), 4.94 (brs, 1H, H-29$_b$), 4.58 (d, J=10.4 Hz, 1H, H-28$_a$), 4.14 (d, J=10.4 Hz, 1H, H-28$_b$), 3.88 (s, 2H, H-30), 3.36 (s, 3H, OCH$_3$), 3.19 (dd, J=10.8 Hz, J=5.1 Hz, 1H, H-3α), 2.68 (s, 3H, CH$_3$-2'), 2.38 (dt, J=11.1 Hz, J=5.3 Hz, 1H, H-19), 1.06 (s, 3H), 1.01 (s, 3H), 0.97 (s, 3H), 0.83 (s, 3H), 0.76 (s, 3H); $^{13}$C NMR (CDCl$_3$, 75 MHz) 150.4 (C20), 149.8 (OCO), 147.9 (C2'), 127.4 (C4'), 118.0 (C5'), 109.6 (C29), 78.8 (C3), 74.9 (C30), 66.7 (C28), 58.3 (OMe); EI-MS m/z (% rel. intensity): 580 (9) M$^+$, 189 (25), 187 (28), 119 (27), 107 (23), 105 (25), 91 (24), 83 (100), 81 (27), 79 (25). And compound 39 (65 mg, 21%): mp (acetone/n-hexane) 116-118° C.; IR (film) $v_{max}$ 3070, 1754, 1642 cm$^{-1}$; $^1$H NMR (CDCl$_3$, 400 MHz) δ 7.36 (brs, 1H, H-5'), 7.34 (brs, 1H, H-5''), 6.87 (brs, 1H, H-4'), 6.86 (s, 1H, H-4''), 4.98 (s, 1H, H-29$_a$), 4.95 (s, 1H, H-29$_b$), 4.65 (dd, J=11.1 Hz, J=4.8 Hz, 1H, H-3α), 4.58 (d, J=10.8 Hz, 1H, H-28$_a$), 4.14 (d, J=10.8 Hz, 1H, H-28$_b$), 3.89 (s, 2H, H-30), 3.37 (s, 3H, OCH$_3$), 2.66 and 2.65 (both s, each 3H, CH$_3$-2', CH$_3$-2''), 2.39 (dt, J=11.3 Hz, J=5.5 Hz, 1H, H-19), 1.08 (s, 3H), 1.03 (s, 3H), 0.96 (s, 3H), 0.95 (s, 3H), 0.90 (s, 3H); $^{13}$C NMR (CDCl$_3$, 100 MHz) δ 150.4 (C20), 149.9 (OCO), 149.5

(OCO), 147.9 (C2' and C2"), 127.9 and 127.7 (C4', C4"), 118.0 (C5' and C5"), 109.8 (C29), 85.9 (C3), 75.1 (C30), 66.5 (C28), 58.4 (OCH); EI-MS m/z (% rel. intensity): 688 (11) M$^+$, 187 (23), 185 (22), 145 (32), 119 (22), 105 (26), 95 (26), 91 (46), 83 (100), 81 (27).

Example 28

3β-hydroxy-30-methoxylup-20(29)-en-28-yl-1H-triazole-1-carboxylate (Compound 37) and 30-methoxylup-20(29)-en-3β,28-di-yl-(1H-triazole-1-carboxylate) (Compound 40)

The method followed that described for compound 16 but using compound 7 (213 mg, 0.45 mmol) and CDT (295 mg, 1.8 mmol) in anhydrous THF (8 ml), at reflux for 7 h. The resulting white solid was purified by FCC eluting with petroleum ether 40-60° C./ethyl acetate (1:1) to afford compound 37 (147 mg, 57%): mp (acetone/n-hexane) 137-140° C.; IR (film) $\upsilon_{max}$ 3414, 3070, 1782, 1766, 1645 cm$^{-1}$; $^1$H NMR (CDCl$_3$, 300 MHz) δ 8.82 (brs, 1H, H-5'), 8.09 (brs, 1H, H-3'), 4.97 (brs, 1H, H-29$_a$), 4.94 (brs, 1H, H-29$_b$), 4.72 (d, J=10.6 Hz, 1H, H-28$_a$), 4.29 (d, J=10.6 Hz, 1H, H-28$_b$), 3.88 (s, 2H, H-30), 3.36 (s, 3H, OCH$_3$), 3.19 (dd, J=10.8 Hz, J=5.0 Hz, H-3α), 2.39 (dt, J=11.2 Hz, J=5.3 Hz, 1H, H-19), 1.06 (s, 3H), 1.01 (s, 3H), 0.97 (s, 3H), 0.83 (s, 3H), 0.76 (s, 3H); $^{13}$C NMR (CDCl$_3$, 75 MHz) δ 153.6 (C3'), 150.3 (C20), 147.9 (OCO), 145.4 (C5'), 109.7 (C29), 78.9 (C3), 74.9 (C30), 68.1 (C28), 58.3 (OCH$_3$); EI-MS m/z (% rel. intensity): 567 (13) M$^+$, 201 (71), 189 (78), 187 (70), 145 (72), 131 (61), 119 (71), 105 (82), 91 (100), 79 (57). And compound 40 (52 mg, 17%): mp (acetone/n-hexane) 172-175° C.; IR (film) $\upsilon_{max}$ 3070, 1782, 1763, 1646 cm$^{-1}$; $^1$H NMR (CDCl$_3$, 300 MHz) δ 8.83 and 8.79 (both s, each 1H, H-5', H-5"), 8.09 and 8.08 (both s, each 1H, H-3', H-3"), 4.98 (brs, 1H, H-29$_a$), 4.96 (brs, 1H, H-29$_b$), 4.82-4.71 (m, 2H, H-3α and H-28$_a$), 4.29 (d, J=10.8 Hz, 1H, H-28$_b$), 3.89 (s, 2H, H-30), 3.37 (s, 3H, OCH$_3$), 2.40 (dt, J=11.1 Hz, J=5.4 Hz, 1H, H-19), 1.09 (s, 3H), 1.03 (s, 3H), 0.99 (s, 3H), 0.98 (s, 3H), 0.91 (s, 3H); $^{13}$C NMR (CDCl$_3$, 75 MHz) δ 153.6 and 153.5 (C3', C3"), 150.3 (C20), 147.9 (OCO), 147.2 (OCO), 145.4 and 145.3 (C5', C5"), 109.8 (C29), 87.7 (C3), 74.9 (C30), 68.1 (C28), 58.3 (OCH$_3$); EI-MS m/z (% rel. intensity): 663 (15) M$^+$, 201 (70), 119 (81), 107 (66), 105 (80), 95 (75), 91 (100), 81 (94), 79 (82), 67 (74).

Example 29

3β-hydroxy-(20R)-lupan-29-oxo-28-yl-1H-imidazole-1-carboxylate (Compound 41) and (20R)-lupane-29-oxo-3β,28-di-yl-(1H-imidazole-1-carboxylate) (Compound 43)

The method followed that described for compound 14 but using compound 9 (298 mg, 0.65 mmol) and CDI (316 mg, 1.95 mmol) in anhydrous THF (12 ml), at reflux for 7 h. The resulting white solid was purified by FCC eluting with petroleum ether 40-60° C./ethyl acetate (2:3) to afford compound 41 (239 mg, 67%): mp (acetone/n-hexane) 175-177° C.; IR (film) $\upsilon_{max}$ 3414, 1762, 1722, 1239 cm$^{-1}$; $^1$H NMR (CDCl$_3$, 400 MHz) δ 9.85 (d, J=1.9 Hz, 1H, H-29), 8.15 (brs, 1H, H-2'), 7.42 (brs, 1H, H-5'), 7.09 (brs, 1H, H-4'), 4.60 (d, J=10.9 Hz, 1H, H-28$_a$), 4.13 (d, J=10.9 Hz, 1H, H-28$_b$), 3.21 (dd, J=10.8 Hz, J=5.1 Hz, 1H, H-3α), 2.64 (m, 1H, H-20), 1.15 (d, J=7.0 Hz, 3H, H-30), 1.07 (s, 3H), 0.98 (s, 6H), 0.85 (s, 3H), 0.77 (s, 3H); $^{13}$C NMR (CDCl$_3$, 100 MHz) δ 206.3 (C29), 149.1 (OCO), 137.0 (C2'), 130.6 (C4'), 117.1 (C5'), 78.8 (C3), 66.4 (C28), 48.8 (C20), 14.4 (C30); EI-MS m/z (% rel. intensity): 552 (18) M$^+$, 207 (46), 189 (58), 187 (47), 145 (49), 119 (45), 105 (51), 91 (58), 79 (48), 69 (100). And compound 43 (128 mg, 30%): mp (acetone/n-hexane) 145-146° C.; IR (film) $\upsilon_{max}$ 1758, 1716, 1239 cm$^{-1}$; $^1$H NMR (CDCl$_3$, 300 MHz) δ 9.85 (d, J=1.9 Hz, 1H, H-29), 8.15 (brs, 2H, H-2', H-2"), 7.43 (brs, 2H, H-5', H-5"), 7.09 (brs, 2H, H-4', H-4"), 4.69 (dd, J=10.9 Hz, J=5.4 Hz, 1H, H-3α), 4.61 (d, J=10.9 Hz, 1H, H-28$_a$), 4.13 (d, J=10.9 Hz, 1H, H-28$_b$), 2.64 (m, 1H, H-20), 1.16 (d, J=7.0 Hz, 3H, H-30), 1.09 (s, 3H), 0.99 (s, 3H), 0.97 (s, 6H), 0.92 (s, 3H); $^{13}$C NMR (CDCl$_3$, 75 MHz) δ 206.1 (C29), 148.9 (OCO), 148.4 (OCO) 136.9 (C2', C2"), 130.6 (C4', C4"), 117.0 (C5', C5"), 86.2 (C3), 66.3 (C28); EI-MS m/z (% rel. intensity): 646 (6) M$^+$, 187 (23), 159 (23), 119 (23), 105 (29), 93 (20), 91 (34), 81 (19), 79 (22), 69 (100).

Example 30

3β-hydroxy-(20R)-lupan-29-oxo-28-yl-2'-methyl-1H-imidazole-1-carboxylate (Compound 42)

The method followed that described for compound 15 but using compound 9 (194 mg, 0.42 mmol) and CBMI (148 mg, 0.84 mmol) in anhydrous THF (8 ml), at reflux for 6 h. The resulting white solid was purified by FCC eluting with petroleum ether 40-60° C./ethyl acetate (3:2) to afford compound 42 (179 mg, 75%): mp (acetone/n-hexane) 132-134° C.; IR (film) $\upsilon_{max}$ 3365, 1759, 1716, cm$^{-1}$; $^1$H NMR (CDCl$_3$, 300 MHz) δ 9.85 (d, J=1.8 Hz, 1H, H-29), 7.35 (d, J=1.7 Hz, 1H, H-5'), 6.87 (d, J=1.7 Hz, 1H, H-4'), 4.55 (d, J=10.9 Hz, 1H, H-28$_a$), 4.09 (d, J=10.9 Hz, 1H, H-28$_b$), 3.21 (dd, J=10.4 Hz, J=4.6 Hz, 1H, H-3α), 2.66 (s, 3H, CH$_3$-2'), 1.16 (d, J=7.0 Hz, 3H, H-30), 1.07 (s, 3H), 0.98 (s, 6H), 0.85 (s, 3H), 0.77 (s, 3H); $^{13}$C NMR (CDCl$_3$, 75 MHz) δ 206.3 (C29), 149.2 (OCO), 144.3 (C2'), 130.1 (C4'), 118.1 (C5'), 78.9 (C3), 66.0 (C28); EI-MS m/z (% rel. intensity): 566 (8) M+, 189 (67), 161 (72), 147 (72), 133 (83), 105 (80), 91 (93), 83 (68), 81 (100), 79 (62).

Example 31

28-(1H-imidazol-1-yl)-lup-20(29)-en-3,28-dione (Compound 44)

The method followed that described for compound 14 but using compound 11 (205 mg, 0.45 mmol) and CDI (219 mg, 1.35 mmol) in anhydrous THF (8 ml), at reflux for 9 h. The crude product was purified by FCC eluting with petroleum ether 40-60° C./ethyl acetate (3:2) to yield compound 44 (203 mg, 89%): mp (benzene) 189-190° C.; IR (film) $\upsilon_{max}$ 3073, 1721, 1703, 1642 cm$^{-1}$; $^1$H NMR (CDCl$_3$, 300 MHz) δ 8.28 (s, 1H, H-2'), 7.54 (s, 1H, H-5'), 7.05 (s, 1H, H-4'), 4.78 (s, 1H, H-29$_a$), 4.65 (s, 1H, H-29$_b$), 2.97 (dt, J=10.7 Hz, J=4.2 Hz, 1H, H-19), 1.71 (s, 3H, H-30), 1.06 (s, 3H), 1.01 (brs, 6H), 0.96 (s, 3H), 0.94 (s, 3H); $^{13}$C NMR (CDCl$_3$, 75 MHz) δ 217.9 (C3), 172.9 (C28), 149.7 (C20), 137.3 (C2'), 129.6 (C4'), 117.4 (C5'), 110.2 (C29); EI-MS m/z (% rel. intensity): 504 (4) M$^+$, 410 (30), 409 (100), 245 (46), 203 (49), 189 (58), 147 (25), 107 (31), 105 (27), 91 (24).

Example 32

28-(2'-methyl-1H-imidazol-1-yl)-lup-20(29)-en-3,28-dione (Compound 45)

The method followed that described for compound 15 but using compound 11 (205 mg, 0.45 mmol) and CBMI (238 mg, 1.35 mmol) in anhydrous THF (8 ml), at reflux for 8 h.

The crude product was purified by FCC eluting with petroleum ether 40-60° C./ethyl acetate (3:2) to yield compound 45 (197 mg, 84%): mp (acetone/n-hexane) 196-198° C.; IR (film) $\upsilon_{max}$ 3073, 1721, 1703, 1642 cm$^{-1}$; $^1$H NMR (CDCl$_3$, 300 MHz) δ 7.40 (d, J=1.5 Hz, 1H, H-5'), 6.86 (d, J=1.5 Hz, 1H, H-4'), 4.78 (brs, 1H, H-29$_a$), 4.65 (brs, 1H, H-29$_b$), 3.06 (dt, J=11.1 Hz, J=4.6 Hz, 1H, H-19), 2.63 (s, 3H, CH$_3$-2'), 1.72 (s, 3H, H-30), 1.06 (s, 3H), 1.02 (s, 3H), 1.00 (s, 3H), 0.98 (s, 3H), 0.94 (s, 3H); $^{13}$C NMR (CDCl$_3$, 75 MHz) δ 218.0 (C3), 175.2 (C28), 149.9 (C20), 148.9 (C2'), 126.9 (C4'), 117.9 (C5'), 110.0 (C29); EI-MS m/z (% rel. intensity): 518 (2) M$^+$, 409 (100), 245 (54), 203 (50), 189 (76), 119 (50), 105 (58), 91 (71), 81 (72), 79 (49).

Example 33

28-(1H-imidazol-1-yl)-lup-1,20 (29)-dien-3,28-dione (Compound 46)

The method followed that described for compound 14 but using compound 12 (204 mg, 0.45 mmol) and CDI (219 mg, 1.35 mmol) in anhydrous THF (8 ml), at reflux for 9 h. The crude product was purified by FCC eluting with petroleum ether 40-60° C./ethyl acetate (3:2) to yield compound 46 (186 mg, 82%): mp (acetone/n-hexane) 95-96° C.; IR (film) $\upsilon_{max}$ 3070, 1762, 1720, 1668, 1645 cm$^{-1}$; $^1$H NMR (CDCl$_3$, 300 MHz) δ 8.29 (s, 1H, H-2'), 7.54 (s, 1H, H-5'), 7.12 (d, J=10.1 Hz, 1H, H-1), 7.05 (s, 1H, H-4'), 5.80 (d, J=10.1 Hz, 1H, H-2), 4.79 (s, 1H, H-29$_a$), 4.67 (s, 1H, H-29$_b$), 2.98 (dt, J=11.0 Hz, J=4.6 Hz, 1H, H-19), 1.72 (s, 3H, H-30), 1.12 (s, 3H), 1.07 (s, 6H), 1.01 (s, 3H), 1.00 (s, 3H); $^{13}$C NMR (CDCl$_3$, 75 MHz) δ 205.4 (C3), 172.6 (C28), 159.6 (C1), 149.5 (C20), 137.1 (C2'), 128.8 (C4'), 125.2 (C2), 117.5 (C5'), 110.3 (C29); EI-MS m/z (% rel. intensity): 502 (4) M$^+$, 408 (32), 407 (100), 243 (43), 205 (30), 203 (26), 189 (34), 135 (25), 105 (28), 91 (29).

Example 34

28-(2'-methyl-1H-imidazol-1-yl)-lup-1,20(29)-dien-3,28-dione (Compound 47)

The method followed that described for compound 15 but using compound 12 (204 mg, 0.45 mmol) and CBMI (2.38 mg, 1.35 mmol) in anhydrous THF (8 ml), at reflux for 9 h. The crude product was purified by FCC eluting with petroleum ether 40-60° C./ethyl acetate (3:1) to yield compound 47 (202 mg, 87%): mp (acetone/n-hexane) 99-103° C.; IR (film) $\upsilon_{max}$ 3073, 1760, 1721, 1668, 1642 cm$^{-1}$; $^1$H NMR (CDCl$_3$, 300 MHz) δ 7.42 (brs, 1H, H-5'), 7.12 (d, J=10.3 Hz, 1H, H-1), 6.90 (brs, 1H, H-4'), 5.80 (d, J=10.3 Hz, 1H, H-2), 4.80 (s, 1H, H-29$_b$), 4.67 (s, 1H, H-29$_b$) 3.06 (dt, J=10.8 Hz, J=4.3 Hz, 1H, H-19), 2.67 (s, 3H, CH$_3$-2), 1.73 (s, 3H, H-30), 1.12 (s, 3H), 1.07 (s, 6H), 1.01 (s, 6H); $^{13}$C NMR (CDCl$_3$, 75 MHz) δ 205.4 (C3), 175.0 (C28), 159.6 (C1), 149.6 (C20), 148.9 (C2'), 126.4 (C4'), 125.1 (C2), 118.0 (C5'), 110.1 (C29); EI-MS m/z (% rel. intensity): 516 (3) M$^-$, 408 (37), 407 (100), 243 (56), 205 (37), 189 (42), 135 (43), 105 (37), 91 (44), 81 (36).

Example 35

2-hydroxy-28-(1H-imidazol-1-yl)-lup-1,20(29)-dien-3,28-dione (Compound 48) and 2-(1H-imidazole-1-carbonyloxy)-28-(1H-imidazol-1-yl)-lup-1,20(29)-dien-3,28-dione (Compound 49)

The method followed that described for compound 14 but using compound 13 (304 mg, 0.65 mmol) and CDI (524 mg, 3.25 mmol) in anhydrous THF (12 ml), at reflux for 8 h. The resulting white solid was purified by FCC eluting with petroleum ether 40-60° C./ethyl acetate (1:4) to afford compound 48 (237 mg, 70%): mp (acetone/n-hexane) 145-148° C.; IR (film) $\upsilon_{max}$ 3448, 3078, 1762, 1724, 1667, 1645 cm$^{-1}$; $^1$H NMR (CDCl$_3$, 400 MHz) δ 8.43 (s, 1H, H-2'), 7.56 (s, 1H, H-5'), 7.09 (s, 1H, H-4'), 6.45 (s, 1H, H-1), 4.79 s, 1H, H-29), 4.67 (s, 1H, H-29$_b$), 2.97 (dt, J=10.6 Hz, J=4.0 Hz, 1H, H-19), 1.72 (s, 1H, H-30), 1.19 (s, 3H), 1.14 (s, 3H), 1.10 (s, 3H), 0.99 (brs, 6H); $^{13}$C NMR (CDCl$_3$, 100 MHz) δ 201.1 (C3), 172.9 (C28), 149.5 (C20), 143.9 (C2), 137.3 (C2'), 129.6 (C4'), 128.8 (C1), 117.4 (C5'), 110.4 (C29); EI-MS m/z (% rel. intensity): 518 (22) M$^+$, 423 (100), 215 (94), 213 (65), 189 (57), 119 (55), 1.05 (54), 91 (89), 79 (54), 69 (55). And compound 49 (109 mg, 27%): mp (acetone/n-hexane) 211-213° C.; IR (film) $\upsilon_{max}$ 3070, 1826, 1757, 1721, 1642 cm$^{-1}$; $^1$H NMR (CDCl$_3$, 300 MHz) δ 8.42 and 8.27 (both s, each 1H, H-2', H-2''), 7.79 and 7.51 (both s, each 1H, H-5', H-5''), 7.21 and 7.04 (both s, each 1H, H-4', H-4''), 6.97 (s, 1H, H-1), 4.74 (brs, 1H, H-29$_a$), 4.67 (brs, 1H, H-29$_b$), 2.92 (dt, J=10.9 Hz, J=4.6 Hz, 1H, H-19), 1.73 (s, 3H, H-30), 1.36 (s, 3H), 1.17 (s, 3H), 1.16 (s, 3H), 1.00 (s, 3H), 0.89 (s, 3H); $^{13}$C NMR (CDCl$_3$, 75 MHz) δ 202.3 (C3), 172.8 (C28), 152.2 (C20), 149.1 (OCO), 146.5 (C2), 137.2 (C2' and C2''), 132.6 (C1) 129.6 (C4' and C4''), 117.3 (C5' and C5''), 110.6 (C29); EI-MS m/z (% rel. intensity): 612 (9) M$^+$, 518 (35), 517 (100), 449 (19), 405 (14), 295 (15), 189 (27), 105 (18), 91 (21), 69 (16)

Example 36

2-(2'-methyl-1H-imidazole-1-carbonyloxy)-3-oxo-lup-1,20(29)-dien-28-oic acid (Compound 50)

The method followed that described for compound 15 but using compound 13 (210 mg, 0.45 mmol) and CBMI (396 mg, 2.25 mmol) in anhydrous THF (8 ml), at reflux for 7 h. The resulting white solid was purified by FCC eluting with petroleum ether 40-60° C./ethyl acetate (2:3) to afford compound 50 (215 mg, 83%): nip (acetone/n-hexane) 141-143° C.; IR (film) $\upsilon_{max}$ 3394, 3070, 1824, 1770, 1687, 1645, cm$^{-1}$; $^1$H NMR(CDCl$_3$, 400 MHz) δ 7.41 (d, J=1.7 Hz, 1H, H-5'), 6.99 (s, 1H, H-1), 6.92 (d, J=1.7 Hz, 1H, H-4'), 4.75 (s, 1H, H-29$_a$), 4.62 (s, 1H, H-29$_b$), 3.04 (dt, J=10.9 Hz, J=4.0 Hz, 1H, H-19), 2.66 (s, 3H, CH$_3$-2'), 1.69 (s, 3H, H-30), 1.24 (s, 3H), 1.21 (s, 3H), 1.16 (s, 3H), 1.05 (s, 3H), 1.01 (s, 3H); $^{13}$C NMR (CDCl$_3$, 100 MHz) δ 196.9 (C3), 180.7 (C28), 150.2 (C20), 148.6 (OCO), 147.4 (C2), 145.7 (C2'), 142.0 (C1), 127.6 (C4'), 118.4 (C5'), 109.8 (C29); EI-MS m/z (% rel. intensity): 576 (3) M$^+$, 215 (100), 213 (62), 107 (35), 105 (46), 93 (35), 91 (62), 81 (34), 79 (40), 67 (34).

Screening of Antiproliferative Activity

Figure 7:
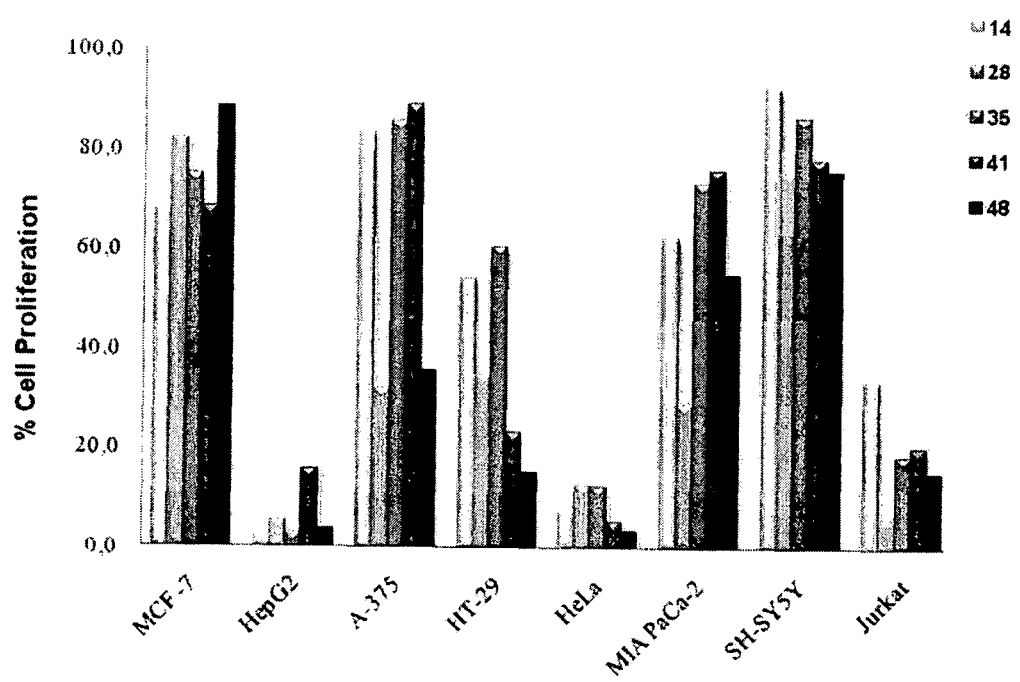
FIG. 7 represents the screening of antiproliferative activity of different triterpene derivatives of the present invention on human cancer cell lines.

Compounds 14, 28, 35, 41 and 48 were screening for antiproliferative activity against the following cancer cell lines: MCF-7 (human breast adenocarcinoma), HepG2 (human hepatocellular carcinoma), A-375 (human melanoma), HT-29 (human colon adenocarcinoma), HeLa (human cervical adenocarcinoma), MIA-PaCa-2 (human pancreas adenocarcinoma), SH-SY5Y (human neuroblastoma), and Jurkat (human leukemia) (FIG. 7). For this screening, cell suspensions were prepared and diluted according to the particular cell type and the expected target cell density (1×10$^3$–30×10$^3$ cells/well based on the cell growth characteristics). Cells were plated in 96-well plates and cell viability was determined by the MTT assay (MCF-7, HepG2, A-375, HT-29, HeLa and MIA-PaCa-2) or XTT assay (SH-SY5Y and Jurkat) after 72 h of incubation with the compounds at the concentration of 20 μM, in triplicate.

Cytotoxic Activity Against HepG2, HeLa, Jurkat and Chang Liver Cell Lines

The cytotoxic of compounds of formulas (I) and (II) 14-50 was assessed towards human cancer (HepG2, HeLa and Jurkat) cell lines (Table 3 below). Compounds presented on Table 4 were also tested against a non-tumoral liver cell line (Chang liver). The cell viability of HeLa, HepG2 and Chang liver cells was determined by the MTT assay. Briefly, exponentially growing cells were plated in 96-well plates at a density of $1 \times 10^3$, $8 \times 10^3$ and $5 \times 10^3$ cells/well respectively and incubated for 24 h before treatment. The grown medium was replaced with one contained the tested compounds dissolved in DMSO (final DMSO concentration <0.1%) at different concentrations, in triplicate wells, and cells were incubated for 72 h. After incubation with the compounds, the medium was removed and MTT solution (0.5 mg/ml, 100 μl) was added to each well and the plates were incubated again for 1 h. DMSO (100 μl) was then added to dissolve the formazan crystals and the plates were immediately read at 550 nm on an ELISA plate reader (Tecan Sunrise MR20-301, TECAN, Austria). For the Jurkat cells, the cell viability was determined by the XTT assay. Briefly, exponentially growing cells were plated in 96-well plates at a density of $5.5 \times 10^3$ cells/well, treated with different concentrations of compounds in triplicate and incubated for 72 h. After incubation with the compounds the XTT labeling mixture (100 μl) were added to each of the wells and after a 4 h incubation period the plates were read at 450 nm on an ELISA plate reader. Results presented in Tables 3 and 4 below express the concentration inhibiting 50% of the cell growth ($IC_{50}$). Known for its cytotoxic activity, betulinic acid 2 was used as a positive control in this experimentation. Based on the $IC_{50}$ values, compounds with $IC_{50}$<10 μM were considered strongly active, those with $IC_{50}$ ranging from 10 to 30 μM were considered moderately active and those with $IC_{50}$>30 μM were considered weakly active. All the $IC_{50}$ results represent an average of a minimum of three experiments and were expressed as means±standard deviation (SD).

TABLE 3

In vitro cytotoxic activity of lupane derivatives

| Compound | $IC_{50}$ (μM ±SD)[a] | | |
|---|---|---|---|
| | HepG2[b] | Jurkat[c] | HeLa[d] |
| 2 | 36.4 ± 1.5 | 26.9 ± 2.2 | 26.0 ± 2.1 |
| 14 | 4.2 ± 0.3 | 16.3 ± 1.2 | 7.6 ± 0.6 |
| 15 | 8.1 ± 0.4 | 15.8 ± 2.4 | 11.0 ± 1.7 |
| 16 | — | — | 15.2 ± 2.1 |
| 17 | >30 | >30 | >30 |
| 18 | >30 | >30 | >30 |
| 19 | — | — | >30 |
| 20 | 2.0 ± 0.4 | 11.1 ± 1.3 | 3.0 ± 0.2 |
| 21 | — | — | 11.3 ± 1.9 |
| 22 | >30 | >30 | >30 |
| 23 | >30 | >30 | >30 |
| 24 | — | — | 23.2 ± 2.1 |
| 25 | >30 | >30 | >30 |
| 26 | >30 | >30 | >30 |
| 27 | — | — | >30 |
| 28 | 6.2 ± 0.2 | 5.2 ± 0.7 | 5.1 ± 0.3 |
| 29 | 7.3 ± 1.0 | 16.1 ± 3.3 | 7.5 ± 1.5 |
| 30 | 2.9 ± 0.4 | 6.0 ± 1.2 | 8.2 ± 0.4 |
| 31 | 11.6 ± 0.8 | 20.1 ± 3.2 | 12.4 ± 1.7 |

TABLE 3-continued

In vitro cytotoxic activity of lupane derivatives

| Compound | $IC_{50}$ (μM ±SD)[a] | | |
|---|---|---|---|
| | HepG2[b] | Jurkat[c] | HeLa[d] |
| 32 | — | — | 14.5 ± 3.2 |
| 33 | 4.3 ± 0.1 | 9.9 ± 0.6 | 8.2 ± 0.5 |
| 34 | 13.4 ± 1.7 | 16.4 ± 2.4 | 13.4 ± 1.7 |
| 35 | 8.3 ± 0.4 | 12.2 ± 1.3 | 9.8 ± 0.6 |
| 36 | 14.4 ± 1.3 | 24.8 ± 4.7 | 8.9 ± 2.1 |
| 37 | — | — | 13.8 ± 2.3 |
| 38 | 19.6 ± 1.6 | 16.2 ± 1.0 | >30 |
| 39 | 28.2 ± 2.5 | >30 | 13.4 ± 0.6 |
| 40 | — | — | >30 |
| 41 | 11.5 ± 1.1 | 13.7 ± 1.4 | 11.1 ± 1.4 |
| 42 | 14.3 ± 2.4 | 21.3 ± 4.1 | 16.6 ± 1.5 |
| 43 | 26.1 ± 1.1 | 20.2 ± 1.6 | 19.2 ± 1.5 |
| 44 | 0.8 ± 0.05 | 1.4 ± 0.2 | 2.0 ± 0.3 |
| 45 | 5.5 ± 1.1 | 9.3 ± 2.2 | 4.2 ± 1.2 |
| 46 | 1.7 ± 0.2 | 2.3 ± 0.3 | 3.0 ± 0.2 |
| 47 | 12.7 ± 1.2 | 9.4 ± 0.8 | 6.4 ± 0.8 |
| 48 | 6.5 ± 0.4 | 7.0 ± 1.6 | 4.6 ± 0.7 |
| 49 | 4.0 ± 0.3 | 8.1 ± 0.6 | 3.9 ± 0.3 |
| 50 | 6.8 ± 1.5 | 12.5 ± 1.2 | 10.6 ± 0.7 |

[a]Data present mean values (±SD) for three independent experiments made in triplicate
[b]Human hepatocellular carcinoma
[c]Human Leukemia
[d]Human cervical adenocarcinoma

TABLE 4

Table-4 In vitro cytotoxic activity of lupane derivatives against a non-tumoral cell line

| Compound | $IC_{50}$ (μM ±SD)[a] Chang liver[b] |
|---|---|
| 2 | 92.3 ± 4.1 |
| 14 | 79.7 ± 6.4 |
| 20 | 60.7 ± 3.8 |
| 28 | 56.8 ± 2.2 |
| 30 | 149.9 ± 13.6 |
| 33 | 73.9 ± 3.6 |
| 35 | 96.4 ± 7.5 |
| 38 | 170.4 ± 17.7 |
| 41 | 145.7 ± 4.5 |
| 43 | 156.2 ± 12.5 |
| 44 | 48.8 ± 2.8 |
| 46 | 55.9 ± 4.6 |
| 48 | 62.8 ± 10.3 |
| 49 | 71.6 ± 4.9 |

[a]Data present mean values (±SD) for three independent experiments made in triplicate
[b]Human normal liver cells Cell Cycle Analysis of HepG2, HeLA, Jurkat and Chang Liver Treated Cells The effects on the cell cycle of some of these compounds were assessed through flow cytometry by using a fluorescence-activated cell sorter (FACS) (Table 5 below). For this assay $2.3 \times 10^5$ HepG2 cells/well, $2.9 \times 10^4$ HeLa cells/well, $1.6 \times 10^5$ Jurkat cells/well and $1.4 \times 10^5$ Chang liver cells/well were plated in 6 well plates with 2 ml of medium. The number of cells was determined by the relationship number of cells/area wells, considering the number of cells that were cultured in 96-well plates. After 24 h of incubation at 37° C. with 5% $CO_2$, compounds 20, 44, 46 and betulinic acid 2 were added at their respective $IC_{50}$ values. Chang liver cells were incubated with compounds 20, and 46 at concentrations corresponding to the $IC_{80}$ determined for HepG2 at 72 h. Following 72 h. of incubation, cells were harvested by mild trypsinization, collected by centrifugation and stained in ice-cold Tris-buffered saline (TBS), containing 1 mg/ml PI, 10 mg/ml RNAse free of DNAase and 0.1% Igepal CA-630 for 1 h at 4° C. FACS analysis was carried out at 488 nm in an Epics XL flow cytometer (Coulter Corporation, Hialeah, Fla.). Data from $8\times10^3$ cells were collected and analyzed using Multi-cycle program (Phoenix Flow Systems, San Diego, Calif.). All experiments were performed three times with three replicates per experiment. As shown in Table 5 below all the compounds induced significant increase in the population in S phase (increase of 17% for compound 20, 20% for compound 44 and 12% for compound 46 in HepG2 cell line) with a concomitant decrease in the percentage of cells in the G0/G1 phase (decrease of 12% for compound 20, 16% for compound 44 and 7% for compound 46 in HepG2 cell line) with respect to untreated cells, suggesting that these compounds suppress cell proliferation associated with cell-cycle arrest in the S phase. To explore the selectivity of the effect on tumor cells, we also tested compounds 20, 44 and 46 in a non-malignant cell line. Chang liver cells were treated with the compounds at the $IC_{80}$ values determined for HepG2 after 72 h of incubation and no effect was observed, indicating a selective effect of these agents (Table 5 below).

TABLE 5

Cell-cycle analysis of lupane derivatives-treated cells

| Cell line | Compound | Phase of cell cycle (% of cells)[a] | | |
|---|---|---|---|---|
| | | G0/G1 | S | G2/M |
| HepG2[b] | Control | 61.3 ± 2.2 | 19.1 ± 0.5 | 19.5 ± 2.4 |
| | AB | 59.7 ± 2.0 | 25.9 ± 1.3 | 14.3 ± 0.9 |
| | 20 | 49.4 ± 1.2 | 36.1 ± 0.8 | 14.5 ± 0.8 |
| | 44 | 45.6 ± 2.1 | 39.6 ± 3.6 | 14.9 ± 1.4 |
| | 46 | 54.7 ± 1.5 | 30.7 ± 0.6 | 14.3 ± 1.0 |
| HeLa[c] | Control | 69.8 ± 0.7 | 12.9 ± 0.9 | 17.2 ± 0.7 |
| | AB | 66.8 ± 1.2 | 21.4 ± 0.9 | 11.7 ± 1.1 |
| | 20 | 50.6 ± 1.3 | 36.4 ± 2.4 | 13.0 ± 1.4 |
| | 44 | 53.1 ± 1.1 | 33.1 ± 0.9 | 13.8 ± 1.1 |
| | 46 | 64.6 ± 2.4 | 25.6 ± 1.5 | 9.7 ± 1.3 |
| Jurkat[d] | Control | 61.7 ± 4.4 | 13.2 ± 1.9 | 25.1 ± 2.7 |
| | AB | 56.8 ± 5.0 | 18.9 ± 1.2 | 24.1 ± 4.7 |
| | 20 | 48.6 ± 4.4 | 35.6 ± 3.1 | 15.8 ± 2.1 |
| | 44 | 52.7 ± 0.5 | 26.6 ± 0.9 | 20.8 ± 1.1 |
| | 46 | 49.6 ± 2.6 | 29.8 ± 0.8 | 20.7 ± 2.4 |
| Chang liver[e] | Control | 68.2 ± 2.3 | 22.0 ± 1.8 | 9.1 ± 1.4 |
| | 20 | 68.6 ± 4.2 | 22.0 ± 3.0 | 9.3 ± 1.3 |
| | 44 | 68.2 ± 2.9 | 23.2 ± 2.5 | 8.6 ± 0.8 |
| | 46 | 68.2 ± 4.9 | 22.6 ± 3.8 | 9.2 ± 1.4 |

[a]Data present mean values (±SD) for three independent experiments made in triplicate
[b]Human hepatocellular carcinoma
[c]Human Leukemia
[d]Human cervical adenocarcinoma
[e]Human normal liver cells Induction of Apoptosis by Compounds 20, 44 and 46

Figure 8:
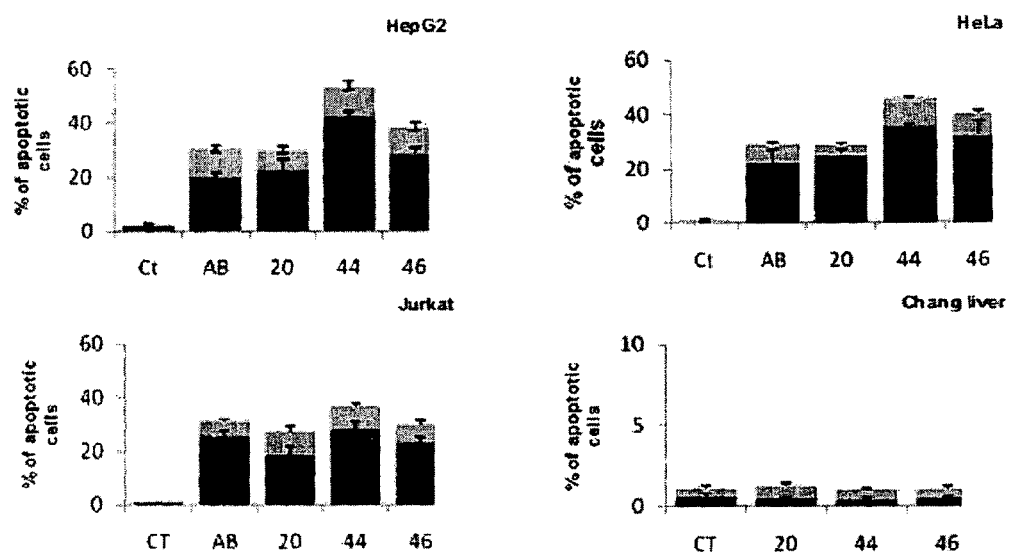
FIG. 8 represents results of the flow cytometric quantification of apoptotic cells after 72 h of incubation with triterpene derivatives 20, 40 and 46 at their respective $IC_{50}$. The percentage of early (dark grey bar) and late (light grey bar) apoptotic cells in each condition is represented as a bars diagram, calculated from dot plots.

Assessment of apoptosis was performed 72 h after treatment with derivatives at their $IC_{50}$. Briefly, the same number of HepG2, HeLa, Jurkat and Chang liver cells as in the cell cycle assay were treated with compounds 20, 44, 46 and betulinic acid 2, as described above. Cells were collected washed once in ice-sold binding buffer (10 mM HEPES/NaOH, pH 7.4, 140 mM NaCl, 2.5 mM $CaCl_2$) and ressuspended in the same buffer (95 µl) at a maximum, of $8\times10^5$ cells/ml. Annexin V-FITC conjugate (1 µg/ml) was added and incubated for 30 min at room temperature in darkness. Just before FACS analysis, cells were stained with 20 µl of mg/ml PI solution. Approximately $1\times10^4$ cells were analysed for each histogram and experiments were performed three times with triplicates per experiment. FACS analysis using Annexin V-FITC staining and PI accumulation was used to differentiate early apoptotic cells (Annexin $V^+$ and $PI^-$) from necrotic or late apoptotic cells (Annexin $V^+$ and $PI^+$). The new lupane derivatives are extremely potent inducers of apoptosis in HepG2, HeLa and Jurkat cells and are markedly more potent that betulinic acid 2 (FIG. 8). In all three cell lines, compound 44 is the most effective at inducing apoptosis, but compound 20 and 46 are also extremely effective (FIG. 8). In comparison with untreated controls, compound 44 treatment of HepG2 cells generated apoptosis in 53% of cells (42% of early apoptosis and 11% of late apoptosis), compound 46 generated apoptosis in 38% of cells (28% of early apoptosis plus 10% late apoptosis) and compound 20 induced apoptosis in 29% of cells (22% of early apoptosis plus 7% late apoptosis) (FIG. 8). At the $IC_{80}$ found for HepG2, no effect on apoptosis induction was observed in the normal liver cell line Chang liver (FIG. 8). These results are in agreement with the lack of inhibition of cell proliferation by these compounds assessed by MTT assay in normal liver cells (Table 4). The introduction of the imidazolyl moiety was important for the induction of apoptosis and the cell cycle arrest, as demonstrated by FACS analysis, since these compounds exhibit more potent apoptotic and cell cycle arrest activity than betulinic acid 2.

Cytotoxicity Against Other Cancer Cell Lines

Compounds presented in Table 6 were also tested in the following cell lines: PC-3 (human prostate adenocarcinoma), LNCaP (human prostate adenocarcinoma), LAPC4 (human prostate adenocarcinoma) and HT-29 (human colon adenocarcinoma).

TABLE 6

In vitro cytotoxic activity of lupane derivatives

| | $IC_{50}$ (µM ±SD)[a] | | | |
|---|---|---|---|---|
| Compound | LAPC4[b] | LNCaP[c] | PC-3[d] | HT-29[e] |
| 14 | 10.3 ± 1.6 | 13.0 ± 1.5 | 21.0 ± 2.0 | — |
| 15 | — | — | — | 16.2 ± 2.1 |
| 17 | 12.9 ± 1.1 | 14.4 ± 1.3 | >30 | — |
| 20 | 16.4 ± 2.1 | 15.0 ± 1.8 | 9.2 ± 0.7 | — |
| 28 | 11.8 ± 0.9 | 15.6 ± 0.8 | 5.6 ± 0.4 | — |
| 29 | — | — | — | 5.7 ± 0.6 |
| 30 | 4.4 ± 0.2 | 1.9 ± 0.2 | 1.1 ± 0.1 | — |
| 31 | — | — | — | 7.8 ± 1.6 |
| 34 | — | — | — | 12.9 ± 0.5 |
| 35 | 9.5 ± 0.7 | 7.7 ± 0.9 | 11.4 ± 1.3 | — |
| 36 | — | — | — | 10.4 ± 1.6 |
| 38 | 7.3 ± 1.1 | 8.1 ± 1.0 | 2.0 ± 0.3 | — |
| 41 | >30 | 15.6 ± 2.4 | 16.7 ± 2.4 | — |
| 42 | — | — | — | 15.8 ± 1.7 |
| 43 | 7.9 ± 1.3 | 6.9 ± 0.3 | 6.2 ± 0.7 | — |
| 44 | 17.2 ± 2.3 | 13.7 ± 0.5 | 6.9 ± 1.1 | — |
| 45 | — | — | — | 4.7 ± 1.1 |
| 47 | — | — | — | 5.9 ± 0.3 |
| 50 | — | — | — | 9.0 ± 1.7 |

[a]Data present mean values (±SD) for three independent experiment made in triplicate
[b]Human prostate adenocarcinoma
[c]Human prostate adenocarcinoma
[d]Human prostate adenocarcinoma
[e]Human colon adenocarcinoma All publications, patents and patent documents are incorporated by reference herein, as though individually incorporated by reference. Although the present invention has been described herein above by way of specific embodiments thereof, it can be modified, without departing from the spirit and nature of the subject invention as defined in the appended claims.

The invention claimed is:

1. A compound of formula (I):

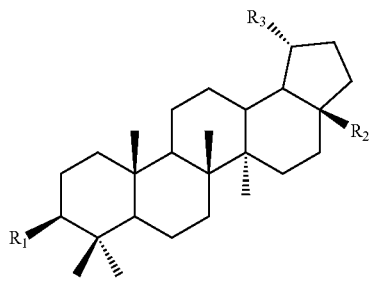

(I)

wherein, in the formula (I), $R_1$, $R_2$ and $R_3$ have the following meanings:

| Compounds | $R_1$ | $R_2$ | $R_3$ |
|---|---|---|---|
| 14 | OH | CH₂O-C(=O)-imidazole | CH₂=CCH₃ |
| 15 | OH | CH₂O-C(=O)-(2-methyl)imidazole | CH₂=CCH₃ |
| 16 | OH | CH₂O-C(=O)-triazole | CH₂=CCH₃ |
| 17 | O-C(=O)-imidazole | CH₂O-C(=O)-imidazole | CH₂=CCH₃ |
| 18 | O-C(=O)-(2-methyl)imidazole | CH₂O-C(=O)-(2-methyl)imidazole | CH₂=CCH₃ |
| 19 | O-C(=O)-triazole | CH₂O-C(=O)-triazole | CH₂=CCH₃ |
| 20 | O-C(=O)-imidazole | CH₂OH | CH₂=CCH₃ |
| 21 | O-C(=O)-triazole | CH₂OH | CH₂=CCH₃ |
| 22 | OAc | CH₂O-C(=O)-imidazole | CH₂=CCH₃ |
| 23 | OAc | CH₂O-C(=O)-(2-methyl)imidazole | CH₂=CCH₃ |
| 24 | OAc | CH₂O-C(=O)-triazole | CH₂=CCH₃ |
| 25 | O-C(=O)-imidazole | CH₂OAc | CH₂=CCH₃ |
| 26 | O-C(=O)-(2-methyl)imidazole | CH₂OAc | CH₂=CCH₃ |
| 27 | O-C(=O)-triazole | CH₂OAc | CH₂=CCH₃ |
| 28 | O-C(=O)-imidazole | COOH | CH₂=CCH₃ |
| 29 | O-C(=O)-(2-methyl)imidazole | COOH | CH₂=CCH₃ |
| 30 | O-C(=O)-imidazole | C(=O)-imidazole | CH₂=CCH₃ |
| 31 | O-C(=O)-(2-methyl)imidazole | C(=O)-(2-methyl)imidazole | CH₂=CCH₃ |
| 32 | O-C(=O)-triazole | C(=O)-triazole | CH₂=CCH₃ |

-continued

| Compounds | R₁ | R₂ | R₃ |
|---|---|---|---|
| 33 | C(=O)O-(1-imidazolyl) | COOMe | CH₂=CCH₃ |
| 34 | C(=O)O-(2-methyl-1-imidazolyl) | COOMe | CH₂=CCH₃ |
| 35 | OH | CH₂O-C(=O)-(1-imidazolyl) | CH₂=CCH₂OMe |
| 36 | OH | CH₂O-C(=O)-(2-methyl-1-imidazolyl) | CH₂=CCH₂OMe |
| 37 | OH | CH₂O-C(=O)-(1-(1,2,4-triazolyl)) | CH₂=CCH₂OMe |
| 38 | C(=O)O-(1-imidazolyl) | CH₂O-C(=O)-(1-imidazolyl) | CH₂=CCH₂OMe |

-continued

| Compounds | R₁ | R₂ | R₃ |
|---|---|---|---|
| 39 | C(=O)O-(2-methyl-1-imidazolyl) | CH₂O-C(=O)-(2-methyl-1-imidazolyl) | CH₂=CCH₂OMe |
| 40 | C(=O)O-(1-(1,2,4-triazolyl)) | CH₂O-C(=O)-(1-(1,2,4-triazolyl)) | CH₂=CCH₂OMe |
| 41 | OH | CH₂O-C(=O)-(1-imidazolyl) | CH(CH₃)CHO |
| 42 | OH | CH₂O-C(=O)-(2-methyl-1-imidazolyl) | CH(CH₃)CHO |
| 43 | C(=O)O-(1-imidazolyl) | CH₂O-C(=O)-(1-imidazolyl) | CH(CH₃)CHO. |

2. A pharmaceutical composition comprising a therapeutically effective amount of the compound of claim 1, and a pharmaceutically acceptable additive, diluent, carrier, solvent, filler, lubricant, adjuvant, binder, stabilizer or excipient.

\* \* \* \* \*